(12) United States Patent
Hickey et al.

(10) Patent No.: US 6,649,619 B1
(45) Date of Patent: Nov. 18, 2003

(54) COMPOUNDS

(75) Inventors: Deirdre Mary Bernadette Hickey, Harlow (GB); Robert John Ife, Harlow (GB); Colin Andrew Leach, Harlow (GB); Ivan Leo Pinto, Harlow (GB); Stephen Allan Smith, Harlow (GB); Steven James Stanway, Harlow (GB)

(73) Assignee: SmithKline Beecham p.l.c. (GB)

( * ) Notice: Subject to any disclaimer, the term of this patent is extended or adjusted under 35 U.S.C. 154(b) by 0 days.

(21) Appl. No.: 10/357,238

(22) Filed: Feb. 3, 2003

Related U.S. Application Data

(63) Continuation of application No. 09/782,930, filed on Feb. 14, 2001, now abandoned.

(30) Foreign Application Priority Data

Feb. 16, 2000 (GB) .............................................. 0003636
Jan. 19, 2001 (GB) .............................................. 0101437

(51) Int. Cl.[7] ..................... C07D 239/70; A61K 31/517
(52) U.S. Cl. ..................... 514/258.1; 544/253
(58) Field of Search ........................ 544/253; 514/258.1

(56) References Cited

FOREIGN PATENT DOCUMENTS

| WO | WO 99/24420 | 5/1999 |
| WO | WO 00/66567 | 11/2000 |

OTHER PUBLICATIONS

Hickey et al, Chemical Abstracts, vol 135 entry 195570 (2001).*

* cited by examiner

*Primary Examiner*—John M. Ford
(74) *Attorney, Agent, or Firm*—James M Kanagy; Stephen Venetianer; Charles M. Kinzig

(57) ABSTRACT

Pyrimidone compounds of formula (I):

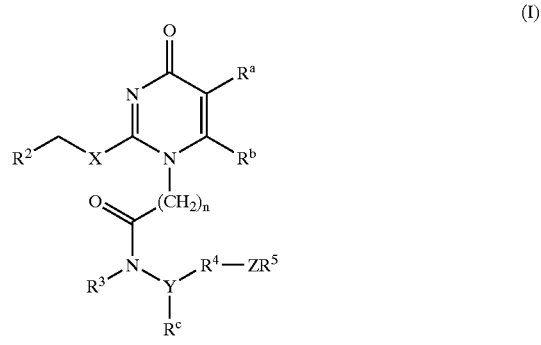

are inhibitors of the enzyme $Lp\text{-}PLA_2$ and are of use in treating atheroscelerosis.

3 Claims, No Drawings

COMPOUNDS

This is a continuation of application Ser. No. 09/782,930 filed Feb. 14, 2001, now abandoned.

The present invention relates to certain novel pyrimidinone compounds, processes for their preparation, intermediates useful in their preparation, pharmaceutical compositions containing them and their use in therapy, in particular in the treatment of atherosclerosis.

WO 95/00649 (SmithKline Beecham plc) describe the phospholipase A2 enzyme Lipoprotein Associated Phospholipase $A_2$ (Lp-$PLA_2$), the sequence, isolation and purification thereof, isolated nucleic acids encoding the enzyme, and recombinant host cells transformed with DNA encoding the enzyme. Suggested therapeutic uses for inhibitors of the enzyme included atherosclerosis, diabetes, rheumatoid arthritis, stroke, myocardial infarction, reperfusion injury and acute and chronic inflammation. A subsequent publication from the same group further describes this enzyme (Tew D et al, Arterioscler Thromb Vas Biol 1996: 16;591–9) wherein it is referred to as LDL-$PLA_2$. A later patent application (WO 95/09921, Icos Corporation) and a related publication in Nature (Tjoelker et al, vol 374, Apr. 6, 1995, 549) describe the enzyme PAF-AH which has essentially the same sequence as Lp-$PLA_2$ and suggest that it may have potential as a therapeutic protein for regulating pathological inflammatory events.

It has been shown that Lp-$PLA_2$ is responsible for the conversion of phosphatidylcholine to lysophosphatidylcholine, during the conversion of low density lipoprotein (LDL) to its oxidised form. The enzyme is known to hydrolyse the sn-2 ester of the oxidised phosphatidylcholine to give lysophosphatidylcholine and an oxidatively modified fatty acid. Both products of Lp-$PLA_2$ action are biologically active with lysophosphatidylcholine, a component of oxidised LDL, known to be a potent chemoattractant for circulating monocytes. As such, lysophosphatidylcholine is thought play a significant role in atherosclerosis by being responsible for the accumulation of cells loaded with cholesterol ester in the arteries. Inhibition of the Lp-$PLA_2$ enzyme would therefore be expected to stop the build up of these macrophage enriched lesions (by inhibition of the formation of lysophosphatidylcholine and oxidised free fatty acids) and so be useful in the treatment of atherosclerosis.

A recently published study (WOSCOPS—Packard et al, N. Engl. J. Med. 343 (2000) 1148–1155) has shown that the level of the enzyme Lp-$PLA_2$ is an independent risk factor in coronary artery disease.

The increased lysophosphatidylcholine content of oxidatively modified LDL is also thought to be responsible for the endothelial dysfunction observed in patients with atherosclerosis. Inhibitors of Lp-$PLA_2$ could therefore prove beneficial in the treatment of this phenomenon. An Lp-$PLA_2$ inhibitor could also find utility in other disease states that exhibit endothelial dysfunction including diabetes, hypertension, angina pectoris and after ischaemia and reperfusion.

In addition, Lp-$PLA_2$ inhibitors may also have a general application in any disorder that involves activated monocytes, macrophages or lymphocytes, as all of these cell types express Lp-$PLA_2$. Examples of such disorders include psoriasis.

Furthermore, Lp-$PLA_2$ inhibitors may also have a general application in any disorder that involves lipid oxidation in conjunction with Lp-$PLA_2$ activity to produce the two injurious products, lysophosphatidylcholine and oxidatively modified fatty acids. Such conditions include the aforementioned conditions atherosclerosis, diabetes, rheumatoid arthritis, stroke, myocardial infarction, reperfusion injury and acute and chronic inflammation.

Patent applications WO 96/12963, WO 96/13484, WO 96/19451, WO 97/02242, WO 97/217675, WO 97/217676, WO 96/41098, and WO 97/41099 (SmithKline Beecham plc) disclose inter alia various series of 4-thionyl/sulfinyl/sulfonyl azetidinone compounds which are inhibitors of the enzyme Lp-$PLA_2$. These are irreversible, acylating inhibitors (Tew et al, Biochemistry, 37, 10087, 1998).

A further class of compounds has now been identified which are non-acylating inhibitors of the enzyme Lp-$PLA_2$. Thus, WO 99/24420 (SmithKline Beecham plc) discloses a class of pyrimidone compounds. International patent applications WO 00/10980, WO 00/66566, WO 00/66567 and WO 00/68208 (SmithKline Beecham plc, published after the priority date of the present application) disclose other classes of pyrimidone compounds. We have now found a further class of pyrimidone compounds which are distinguished by the substitution pattern at the 5 and 6 position of the pyrimidone ring and which have good activity as inhibitors of the enzyme Lp-$PLA_2$.

Accordingly, the present invention provides a compound of formula (I):

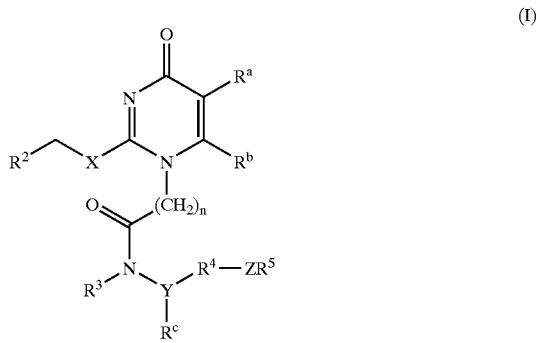

(I)

in which:

$R^a$ is hydrogen, halogen, $C_{(1-3)}$alkyl $C_{(1-3)}$alkoxy, hydroxy$C_{(1-3)}$alkyl, $C_{(1-3)}$alkylthio, $C_{(1-3)}$alkylsulphinyl, amino$C_{(1-3)}$alkyl, mono- or di-$C_{(1-3)}$alkylamino$C_{(1-3)}$alkyl, $C_{(1-3)}$alkylcarbonylamino$C_{(1-3)}$alkyl, $C_{(1-3)}$alkoxy$C_{(1-3)}$alkylcarbonylamino$C_{(1-3)}$alkyl, $C_{(1-3)}$alkylsulphonylamino$C_{(1-3)}$alkyl, $C_{(1-3)}$alkylcarboxy, or $C_{(1-3)}$alkylcarboxy$C_{(1-3)}$alkyl;

$R^b$ is hydrogen, halogen, $C_{(1-3)}$alkyl, or hydroxy$_{(1-3)}$alkyl, with the proviso that $R^a$ and $R^b$ are not simultaneously each hydrogen; or $R^a$ and $R^b$ together are $(CH_2)_n$ where n is 3 or 4, to form, with the pyrimidine ring carbon atoms to which they are attached a fused 5-or 6-membered carbocyclic ring; or $R^a$ and $R^b$ together with the pyrimidine ring carbon atoms to which they are attached form a fused benzo or heteroaryl ring optionally substituted by 1, 2, 3 or 4 substituents which may be the same or different selected from halogen, $C_{(1-4)}$alkyl, cyano, $C_{(1-4)}$alkoxy or $C_{(1-4)}$alkylthio, or mono to perfluoro-$C_{(1-4)}$alkyl);

$R^c$ is hydrogen or $C_{(1-3)}$alkyl;

$R^2$ is an aryl or heteroaryl group, optionally substituted by 1, 2, 3 or 4 substituents which may be the same or different selected from $C_{(1-18)}$alkyl (preferably $C_{(1-6)}$ alkyl), $C_{(1-18)}$alkoxy (preferably $C_{(1-6)}$alkoxy), $C_{(1-18)}$ alkylthio (preferably $C_{(1-6)}$alkylthio), aryl$C_{(1-18)}$alkoxy (preferably aryl$C_{(1-6)}$alkoxy), hydroxy, halogen, CN, $COR^6$, carboxy, $COOR^6$, $NR^6COR^7$, $CONR^8R^9$, $SO_2NR^8R^9$, $NR^6SO_2R^7$, $NR^8R^9$, mono to perfluoro-$C_{(1-4)}$alkyl, mono to perfluoro-$C_{(1-4)}$ alkoxyaryl, and aryl$C_{(1-4)}$alkyl;

$R^3$ is hydrogen, $C_{(1-6)}$alkyl which may be unsubstituted or substituted by 1, 2 or 3 substituents selected from hydroxy, halogen, $OR^6$, $COR^6$, carboxy, $COOR^6$, $CONR^8R^9$, $NR^8R^9$, $NR^8COR^9$, mono- or di-(hydroxy$C_{(1-6)}$alkyl)amino and N-hydroxy$C_{(1-6)}$ alkyl-N—$C_{(1-6)}$alkylamino, for instance, 1-piperidinoethyl; or $R^3$ is Het-$C_{(0-4)}$alkyl in which Het is a 5- to 7- membered heterocyclyl ring comprising N and optionally O or S, bonded through a carbon ring atom and in which N may be substituted by $COR^6$, $COOR^6$, $CONR^8R^9$, or $C_{(1-6)}$ alkyl optionally substituted by 1, 2 or 3 substituents selected from hydroxy, halogen, $OR^6$, $COR^6$, carboxy, $COOR^6$, $CONR^8R^9$ or $NR^8R^9$, for instance, piperidin-4-yl, pyrrolidin-3-yl;

$R^4$ is an aryl or a heteroaryl ring optionally substituted by 1, 2, 3 or 4 substituents which may be the same or different selected from $C_{(1-18)}$alkyl (preferably $C_{(1-6)}$ alkyl), $C_{(1-18)}$alkoxy (preferably $C_{(1-6)}$alkoxy), $C_{(1-18)}$ alkylthio (preferably $C_{(1-6)}$alkylthio), aryl$C_{(1-18)}$alkoxy (preferably aryl$C_{(1-6)}$alkoxy), hydroxy, halogen, CN, $COR^6$, carboxy, $COOR^6$, $NR^6COR^7$, $CONR^8R^9$, $SO_2NR^8R^9$, $NR^6SO_2R^7$, $NR^8R^9$, mono to perfluoro-$C_{(1-4)}$alkyl a perfluoro-$C_{(1-4)}$alkoxy;

$R^5$ is an aryl or heteroaryl ring which is further optionally substituted by 1, 2, 3 or 4 substituents which may be the same or different selected from $C_{(1-18)}$alkyl (preferably $C_{(1-6)}$alkyl), $C_{(1-18)}$alkoxy (preferably $C_{(1-6)}$alkoxy), $C_{(1-18)}$alkylthio (preferably $C_{(1-6)}$alkylthio), aryl$C_{(1-18)}$ alkoxy (preferably aryl$C_{(1-6)}$alkoxy), hydroxy, halogen, CN, $COR^6$, carboxy, $OOR^6$, $CONR^8R^9$, $NR^6COR^7$, $SO_2NR^8R^9$, $NR^6SO_2R^7$, $NR^8R^9$, mono to perfluoro-$C_{(1-4)}$alkyl and mono to perfluoro-$C_{(1-4)}$ alkoxy;

$R^6$ and $R^7$ are independently hydrogen or $C_{(1-20)}$alkyl, for instance $C_{(1-4)}$alkyl (e.g. methyl or ethyl);

$R^8$ and $R^9$ which may be the same or different is each selected from hydrogen, $C_{(1-12)}$alkyl (preferably $C_{(1-6)}$ alkyl); or $R^8$ and $R^9$ together with the nitrogen to which they are attached form a 5- to 7 membered ring optionally containing one or more further heteroatoms selected from oxygen, nitrogen and sulphur, and optionally substituted by one or two substituents selected from hydroxy, oxo, $C_{(1-4)}$alkyl, $C_{(1-4)}$alkylCO, aryl, e.g. phenyl, or aralkyl, e.g benzyl, for instance morpholine or piperazine; or $R^8$ and $R^9$ which may be the same or different is each selected from $CH_2R^{10}$, $CHR^{11}CO_2H$ or a salt thereof in which:

$R^{10}$ is COOH or a salt thereof, $COOR^{12}$, $CONR^6R^7$, CN, $CH_2OH$ or $CH_2OR^6$;

$R^{11}$ is an amino acid side chain such as $CH_2OH$ from serine;

$R^{12}$ is $C_{(1-4)}$alkyl or a pharmaceutically acceptable in vivo hydrolysable ester group;

n is an integer from 1 to 4, preferably 1 or 3, more preferably 1;

X is O or S;

Y is $(CH_2)_p(O)_q$ in which p is 1, 2 or 3 and q is 0 or p is 2 or 3 and q is 1; and Z is O or a bond.

Representative examples of $R^a$ include chloro, bromo, methyl, ethyl, n-propyl, methoxy, hydroxymethyl, hydroxyethyl, methylthio, methylsulphinyl, aminoethyl, dimethylaminomethyl, acetylaminoethyl, 2-(methoxyacetamido)ethyl, mesylaminoethyl, ethylcarboxy, methanesulfonamidoethyl, (methoxyacetamido)ethyl and iso-propylcarboxymethyl.

Representative examples of $R^b$ include hydrogen, and methyl.

Representative examples of $R^a$ and $R^b$ together with the pyrimidine ring carbon atoms to which they are attached forming a fused benzo or heteroaryl ring ring include benzo (to give a quinazolinyl ring), pyrido and thieno, respectively.

Preferably $R^a$ is methyl or ethyl and $R^b$ is hydrogen or methyl, or $R^a$ and $R^b$ together with the pyrimidine ring carbon atoms to which they are attached form a fused 5- or 6-membered carbocyclic ring. More preferably, $R^a$ and $R^b$ together with the pyrimidine ring carbon atoms to which they are attached form a fused 5-membered carbocyclic ring.

Representative examples of $R^c$ include hydrogen and methyl. Preferably, $R^c$ is hydrogen.

Preferably, X is S.

Preferably, Y is $CH_2$.

Preferably, Z is a direct bond.

Representative examples of $R^2$ when an aryl group include phenyl and naphthyl. Representative examples of $R^2$ when a heteroaryl group include pyridyl, pyrimidinyl, pyrazolyl, furanyl, thienyl, thiazolyl, quinolyl, benzothiazolyl, pyridazolyl and pyrazinyl.

Preferably, $R^2$ is an aryl group, optionally substituted by 1, 2, 3 or 4 substituents which may be the same or different selected from $C_{(1-6)}$alkyl, $C_{(1-6)}$alkoxy, $C_{(1-6)}$alkylthio, hydroxy, halogen, CN, mono to perfluoro-$C_{(1-4)}$alkyl, mono to perfluoro-$C_{(1-4)}$alkoxyaryl, and aryl$C_{(1-4)}$alkyl. More preferably, $R^2$ is phenyl optionally substituted by halogen, preferably from 1 to three fluorine atoms, most preferably 4-fluoro.

Preferably, $R^2CH_2X$ is 4-fluorobenzylthio. Representative examples of $R^3$ include hydrogen, methyl, 2-(ethylamino)ethyl, 2-(diethylamino)ethyl, 2-(ethylamino)-2-methylpropyl, 2-(t-butylamino)ethyl, 1-piperidinoethyl, 1-ethyl-piperidin-4-yl.

Preferably, $R^3$ is $C_{(1-3)}$alkyl substituted by a substituent selected from $NR^8R^9$; or $R^3$ is Het-$C_{(0-2)}$alkyl in which Het is a 5- to 7-membered heterocyclyl ring comprising N and in which N may be substituted by $C_{(1-6)}$alkyl. More preferably, $R^3$ is 2-(diethylamino)ethyl.

Representative examples of $R^4$ include phenyl, pyridine and pyrimidine. Preferably, $R^4$ is phenyl.

Representative examples of $R^5$ include phenyl or thienyl, optionally substituted by halogen or trifluoromethyl, preferably at the 4-position. Preferably, $R^5$ is phenyl substituted by trifluoromethyl, preferably at the 4-position.

Preferably, $R^4$ and $R^5$ together form a 4-(phenyl)phenyl, 2-(phenyl)pyrimidinyl or a 2-(phenyl)pyridinyl substituent in which the remote phenyl ring may be optionally substituted by halogen or trifluoromethyl, preferably at the 4-position. More preferably, $R^4$ and $R^5$ together form a 4-(4-trifluoromethylphenyl)phenyl moiety.

It will be appreciated that within the compounds of formula (I) there is a sub-group of compounds which has the formula (IA):

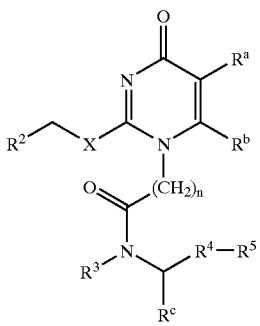

(IA)

in which:
$R^a$, $R^b$, $R^c$, n, $R^2$, $R^3$, $R^4$, $R^5$, and X are as hereinbefore defined; and a further sub-group of compounds which has the formula (IB):

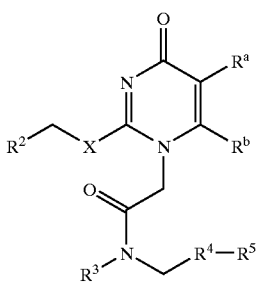

(IB)

in which:
$R^a$, $R^b$, $R^2$, $R^3$, $R^4$, $R^5$, and X are as hereinbefore defined, in particular:
  $R^a$ and $R^b$ together with the pyrimidine ring carbon atoms to which they are attached form a fused 5-membered carbocyclic ring;
  $R^2CH_2X$ is 4-fluorobenzylthio;
  $R^3$ is $C_{(1-3)}$alkyl substituted by $NR^8R^9$; or
  $R^3$ is Het-$C_{(0-2)}$alkyl in which Het is a 5- to 7- membered heterocyclyl ring containing N and in which N may be substituted by $C_{(1-6)}$alkyl.;
  $R^4$ and $R^5$ form a 4-(4-trifluoromethylphenyl)phenyl moiety;
  $R^8$ and $R^9$ which may be the same or different is each selected from hydrogen, or $C_{(1-6)}$alkyl); and
  X is S.

Pharmaceutically acceptable in vivo hydrolysable ester groups for $R^{12}$ include those which break down readily in the human body to leave the parent acid or its salt. Pharmaceutically acceptable in vivo hydrolysable ester groups are well known in the art and examples of such for use in $R^{12}$ are described in WO 00/68208 (SmithKline Beecham).

It will be appreciated that when $R^c$ is $C_{(1-3)}$alkyl, the carbon to which it is attached will be a chiral centre so that diastereoisomers may be formed. In the absence of further chiral centres, these will be enantiomers. The present invention covers all such diastereosiomers and enantiomers, including mixtures thereof.

It will be appreciated that in some instances, compounds of the present invention may include a basic function such as an amino group as a substituent. Such basic functions may be used to form acid addition salts, in particular pharmaceutically acceptable salts. Pharmaceutically acceptable salts include those described by Berge, Bighley, and Monkhouse, *J. Pharm. Sci.*, 1977, 66, 1–19. Such salts may be formed from inorganic and organic acids. Representative examples thereof include maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, taurocholic, benzenesulfonic, p-toluenesulfonic, hydrochloric, hydrobromic, sulfuric, cyclohexylsulfamic, phosphoric and nitric acids.

It will be appreciated that in some instances, compounds of the present invention may include a carboxy group as a substituent. Such carboxy groups may be used to form salts, in particular pharmaceutically acceptable salts. Pharmaceutically acceptable salts include those described by Berge, Bighley, and Monkhouse, *J. Pharm. Sci.*, 1977, 66, 1–19. Preferred salts include alkali metal salts such as the sodium and potassium salts.

When used herein, the term "alkyl" and similar terms such as "alkoxy" includes all straight chain and branched isomers. Representative examples thereof include methyl, ethyl, n-propyl, iso-propyl, n-butyl, sec-butyl, iso-butyl, t-butyl, n-pentyl and n-hexyl.

When used herein, the term "aryl" refers to, unless otherwise defined, a mono- or bicyclic aromatic ring system containing up to 10 carbon atoms in the ring system, for instance phenyl or naphthyl.

When used herein, the term "heteroaryl" refers to a mono- or bicyclic heteroaromatic ring system comprising up to four, preferably 1 or 2, heteroatoms each selected from oxygen, nitrogen and sulphur. Each ring may have from 4 to 7, preferably 5 or 6, ring atoms. A bicyclic heteroaromatic ring system may include a carbocyclic ring.

When used herein, the terms "halogen" and "halo" include fluorine, chlorine, bromine and iodine and fluoro, chloro, bromo and iodo, respectively.

Preferred compounds of formula (I) include:
1-(N-(2-(Diethylamino)ethyl)-N-(4-(4-trifluoromethylphenyl)benzyl)aminocarbonylmethyl)-2-(4-fluorobenzyl)thio-5-ethylpyrimidin-4-one;

1-(N-(2-(Diethylamino)ethyl)-N-(2-(4-trifluoromethylphenyl)pyrid-5-ylmethyl)aminocarbonylmethyl)-2-(4-fluorobenzyl)thio-5-ethylpyrimidin-4-one;

1-(N-(2-(Diethylamino)ethyl)-N-(4-(4-trifluoromethylphenyl)benzyl)aminocarbonylmethyl)-2-(4-fluorobenzyl)thio-5,6-trimethylenepyrimidin-4-one;

1-(N-(2-(Diethylamino)ethyl)-N-(2-(4-trifluoromethylphenyl)pyrid-5-ylmethyl)aminocarbonylmethyl)-2-(4-fluorobenzyl)thio-5,6-trimethylenepyrimidin-4-one; and 1-(N-(2-(Diethylamino)ethyl)-N-(2-(4-trifluoromethylphenyl)pyrimid-5-ylmethyl)aminocarbonylmethyl)-2-(4-fluorobenzyl)thio-5,6-trimethylenepyrimidin-4-one;

or a pharmaceutically acceptable salt thereof;

in particular:
  1-(N-(2-(Diethylamino)ethyl)-N-(4-(4-trifluoromethylphenyl)benzyl)aminocarbonylmethyl)-2-(4-fluorobenzyl)thio-5,6-trimethylenepyrimidinone; or a pharmaceutically acceptable salt thereof.

Since the compounds of the present invention, in particular compounds of formula (I), are intended for use in pharmaceutical compositions, it will be understood that they are each provided in substantially pure form, for example at least 50% pure, more suitably at least 75% pure and preferably at least 95% pure (% are on a wt/wt basis). Impure preparations of the compounds of formula (I) may be used for preparing the more pure forms used in the pharmaceutical compositions. Although the purity of intermediate compounds of the present invention is less critical, it will be readily understood that the substantially pure form is preferred as for the compounds of formula (I). Preferably, whenever possible, the compounds of the present invention are obtained in crystalline form.

When some of the compounds of this invention are allowed to crystallise or are re-crystallised from organic solvents, solvent of crystallisation may be present in the crystalline product. This invention includes within its scope such solvates. Similarly, some of the compounds of this invention may be crystallised or re-crystallised from solvents containing water. In such cases water of hydration may be formed. This invention includes within its scope stoichiometric hydrates as well as compounds containing variable amounts of water that may be produced by processes such as lyophilisation. In addition, different crystallisation conditions may lead to the formation of different polymorphic forms of crystalline products. This invention includes within its scope all polymorphic forms of the compounds of formula (I).

Compounds of the present invention are inhibitors of the enzyme lipoprotein associated phospholipase $A_2$ (Lp-$PLA_2$) and as such are expected to be of use in therapy, in particular in the primary and secondary prevention of acute coronary events, for instance those caused by atherosclerosis, including peripheral vascular atherosclerosis and cerebrovascular atherosclerosis. In a further aspect therefore the present invention provides a compound of formula (I) for use in therapy.

The compounds of formula (I) are inhibitors of lysophosphatidylcholine production by Lp-$PLA_2$ and may therefore also have a general application in any disorder that involves endothelial dysfunction, for example atherosclerosis, diabetes, hypertension, angina pectoris and reperfusion. In addition, compounds of formula (I) may have a general application in any disorder that involves lipid oxidation in conjunction with enzyme activity, for example, in addition to conditions such as atherosclerosis and diabetes, other conditions such as ischaemia, rheumatoid arthritis, stroke, inflammatory conditions of the brain such as Alzheimer's Disease, myocardial infarction, reperfusion injury, sepsis, and acute and chronic inflammation.

Further applications include any disorder that involves activated monocytes, macrophages or lymphocytes, as all of these cell types express Lp-$PLA_2$. Examples of such disorders include psoriasis.

Accordingly, in a further aspect, the present invention provides for a method of treating a disease state associated with activity of the enzyme Lp-$PLA_2$ which method involves treating a patient in need thereof with a therapeutically effective amount of an inhibitor of the enzyme. The disease state may be associated with the increased involvement of monocytes, macrophages or lymphocytes; with the formation of lysophosphatidylcholine and oxidised free fatty acids; with lipid oxidation in conjunction with Lp-$PLA_2$ activity; or with endothelial dysfunction.

Compounds of the present invention may also be of use in treating the above mentioned disease states in combination with an anti-hyperlipidaemic, anti-atherosclerotic, anti-diabetic, anti-anginal, anti-inflammatory, or anti-hypertension agent or an agent for lowering Lp(a). Examples of the above include cholesterol synthesis inhibitors such as statins, anti-oxidants such as probucol, insulin sensitisers, calcium channel antagonists, and anti-inflammatory drugs such as NSAIDs. Examples of agents for lowering Lp(a) include the aminophosphonates described in WO 97/02037, WO 98/28310, WO 98/28311 and WO 98/28312 (Symphar SA and SmithKline Beecham).

It is expected that compounds of the present invention may be used in combination with cholesterol lowering agents, for instance co-administered with a statin. The statins are a well known class of cholesterol lowering agents (HMG-CoA reductase inhibitors) and include atorvastatin, simvarstatin, pravastatin, cerivastatin, fluvastatin, lovastatin and ZD 4522 (also referred to as S4522, Astra Zeneca). The two agents may be administered at substantially the same time or at different times, according to the discretion of the physician.

A substantial minority (approx 30%) of patients with elevated levels of cholesterol are found to not respond to treatment with a statin. In a further use, a compound of the present invention is administered to a patient who has failed to respond to treatment with a statin.

A further preferred combination therapy will be the use of a compound of the present invention and an anti-diabetic agent or an insulin sensitiser, as coronary heart disease is a major cause of death for diabetics. Within this class, preferred compounds for use with a compound of the present invention include the PPARgamma activators, for instance GI262570 (Glaxo Wellcome) and the glitazone class of compounds such as rosiglitazone (Avandia, SmithKline Beecham), troglitazone and pioglitazone.

Preferred indications include primary and secondary prevention of acute coronary events, for instance those caused by atherosclerosis, including peripheral vascular atherosclerosis and cerebrovascular atherosclerosis; adjunctive therapy in prevention of restenosis, and delaying the progression of diabetic/hypertensive renal insufficiency.

In therapeutic use, the compounds of the present invention are usually administered in a standard pharmaceutical composition. The present invention therefore provides, in a further aspect, a pharmaceutical composition comprising a compound of formula (I) and a pharmaceutically acceptable carrier.

Suitable pharmaceutical compositions include those which are adapted for oral or parenteral administration or as a suppository. Compounds of formula (I) which are active when given orally can be formulated as liquids, for example syrups, suspensions or emulsions, tablets, capsules and lozenges. A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent. A composition in the form of a tablet can be prepared using any suitable pharmaceutical carrier(s) routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule. Typical parenteral compositions consist of a solution or suspension of the compound of formula (I) in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration. A typical suppository formulation comprises a compound of formula (I) which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule. Each dosage unit for oral administration contains preferably from 1 to 500 mg (and for parenteral administration contains preferably from 0.1 to 25 mg) of a compound of the formula (I). The daily dosage regimen for an adult patient may be, for example, an oral dose of between 1 mg and 1000 mg, preferably between 1 mg and 500 mg, or an intravenous, subcutaneous, or intra-muscular dose of between 0.1 mg and 100 mg, preferably between 0.1 mg and 25 mg, of the compound of the formula (I), the compound being administered 1 to 4 times per day. Suitably the compounds will be administered for a period of continuous therapy, for example for a week or more.

A compound of formula (I) may be prepared by reacting a compound of formula (II):

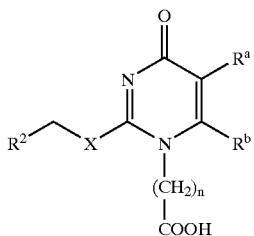

in which X, n, $R^a$, $R^b$ and $R^2$ are as hereinbefore defined, with a compound of formula (III):

$R^5ZR^4$—$YR^cNHR^3$ (III)

in which $R^c$, $R^3$, $R^4$, $R^5$, Y and Z are as hereinbefore defined; under amide forming conditions.

Amide forming conditions are well known in the art, see for instance Comprehensive Organic Synthesis 6, 382–399, and include reacting the acid compound of formula (II) and the amine compound of formula (III) in an inert solvent such as dichloromethane, at ambient temperature, in the presence of a coupling agent. Preferred coupling agents include those developed for use in peptide chemistry, such as 1-(3-dimethylaminopropyl)-3-ethylcarbodiimide hydrochloride ("EDC"), preferably in the presence of an additive such as 1-hydroxybenzotriazole, or O-(7-azabenzotriazol-1-yl)-N,N,N',N'-tetramethyluronium hexafluorophosphate ("HATU"), preferably in the presence of di-isopropylethylamine.

Compounds of formula (I) may also be prepared by a number of other processes, for instance:

(a) reacting a compound of formula (IV):

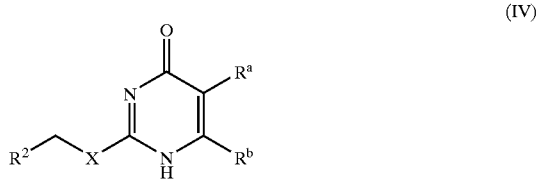

in which X, $R^a$, $R^b$ and $R^2$ are as hereinbefore defined, with a compound of formula (V):

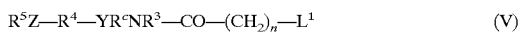

$R^5Z$—$R^4$—$YR^cNR^3$—CO—$(CH_2)_n$—$L^1$ (V)

in which n, $R^3$, $R^4$, $R^5$, $R^c$, Y and Z are as hereinbefore defined, and $L^1$ is a leaving group such as halogen, for instance bromo iodo, or triflate;
in the presence of a base such as a secondary or tertiary amine, for instance di-isopropylethylamine, in an inert solvent such as dichloromethane;

(b) when X is S, reacting a compound of formula (VI):

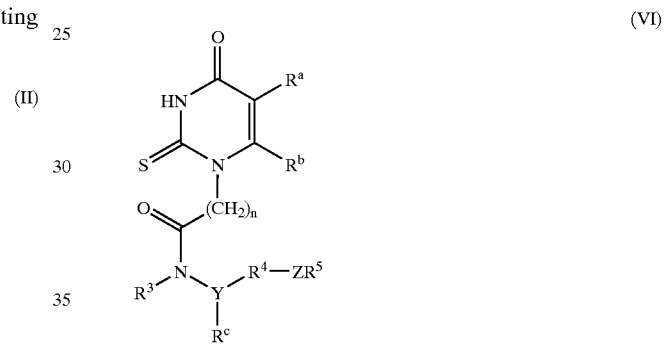

in which n, $R^a$, $R^b$, $R^c$, $R^3$, $R^4$, $R^5$, Y and Z are as hereinbefore defined,
with a compound of formula (VII):

$R^2$—$CH_2$—$L^1$ (VII)

in which $R^2$ and $L^1$ are as hereinbefore defined,
in the presence of a base such as a secondary or tertiary amine, for instance di-isopropylethylamine, in an inert solvent such as dichloromethane; or (c) when X is O, reacting a compound of formula (VIII):

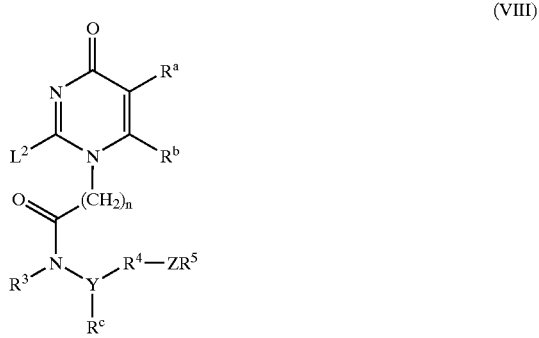

in which n, $R^a$, $R^b$, $R^c$, $R^3$, $R^4$, $R^5$, Y and Z are as hereinbefore defined, and $L^2$ is a leaving group such as halogen or alkylthio, for instance methylthio, with a compound of formula (IX):

$$R^2—CH_2—OH \quad (IX)$$

in which $R^2$ is as hereinbefore defined,
in the presence of a base such as 4-dimethylaminopyridine, in an inert solvent such as pyridine.

It will be appreciated that an initially prepared compound of formula (I) may be converted to another compound of formula (I), by functional group modification, using methods well known to those skilled in the art, for example converting a compound of formula (I) in which $R^a$ is aminoalkyl to a compound of formula (I) in which $R^a$ is alkylcarbonylaminoalkyl, by reaction Compounds of formulae (II), (IV), (VI) and (VIII) for use in the above processes may be prepared by processes illustrated in the following scheme I:

in which:
L$^3$ is a C$_{(1-6)}$ alkyl group, for instance methyl;
R$^{15}$ is a C$_{(1-6)}$ alkyl group, for instance ethyl or t-butyl and L$^1$, L$^2$, R$^a$, R$^b$, R$^c$, R$^2$, R$^3$, R$^4$, R$^5$, n, X, Y and Z are as hereinbefore defined.

With reference to Scheme I:
Amide forming conditions for step (a) are well known in the art. Preferably, the acid of formula (II) is reacted with the amine of formula (III) in an inert solvent, such as dichloromethane, at ambient temperature and in the presence of a coupling agent such as O-(7-azabenzotriazol-1-yl)-N,N,N',N'-tetramethyluronium hexafluorophosphate and di-isopropylethylamine or 1-(3-dimethylaminopropyl)-3-ethylcarbodiimide hydrochloride in the presence of 1-hydroxybenzotriazole.

Alkylation conditions for step (b) include reaction in the presence of a base such as a secondary or tertiary amine, for instance di-isopropylethylamine, in an inert solvent such as

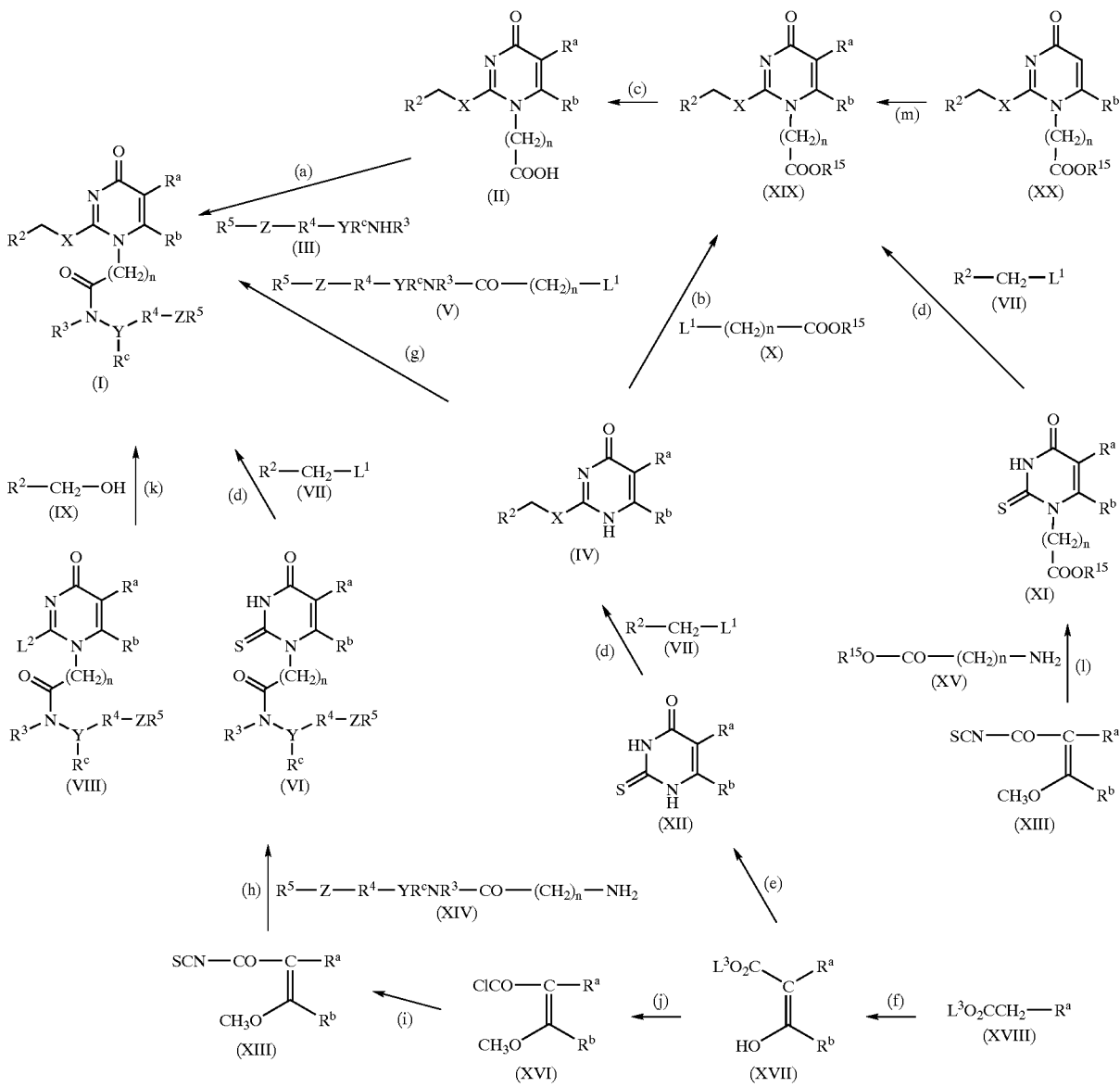

Scheme I

Conditions for step (c) include hydrolysis, for instance using aqueous sodium hydroxide in a solvent such as dioxan or, when $R^{15}$ is t-butyl, dealkylation with an acid such as trifluoroacetic acid in a solvent such as dichloromethane.

Conditions for step (d) include under thioether forming conditions. Advantageously, the reaction is carried out in the presence of a base such as sodium ethoxide or potassium carbonate, preferably in a solvent such as ethanol, dimethyl formamide or acetone, or a secondary or tertiary amine base such as di-isopropylethylamine, in solvent such as dichloromethane.

In step (e), a compound of formula (XVII) is reacted with thiourea, in the presence of sodium ethoxide (preferably generated in situ from sodium and ethanol).

In step (f), a compound of formula (XVIII) is reacted with ethyl formate in the presence of a base such as sodium hydride or potassium iso-propoxide.

In step (g), a compound of formula (IV) is reacted with a compound of formula (V) in the presence of a base such as a secondary or tertiary amine, for instance di-isopropylethylamine, in an inert solvent such as dichloromethane In step (h), a compound of formula (XIII) is reacted with a compound of formula (XIV) in a solvent such as dimethylformamide to form an intermediate thiourea, which is then treated with a base such as sodium methoxide.

In step (i), a compound of formula (XVI) is reacted with a metal thiocyanate, for example potassium thiocyanate, in a solvent such as acetonitrile.

In step (j), a compound of formula (XVII) is reacted with a methylating agent such as dimethyl sulphate in the presence of a base such as potassium carbonate, followed by hydrolysis of the intermediate ester in conventional manner e.g. by basic hydrolysis using sodium hydroxide to give the corresponding carboxylic acid which may then be converted into the acyl chloride, for instance by treatment with oxalyl chloride.

In step (k), a catalyst such as 4-dimethylaminopyridine, and in a solvent such as pyridine are used.

In step (l), a compound of formula (XIII) is reacted with a compound of formula (XV) in a solvent such as dimethylformamide to form an intermediate thiourea, which is then treated with a base such as sodium methoxide.

In step (m) a compound of formula (XX) is converted to a compound of formula (XIX), in which $R^a$ is halogen, by treatment with N-halosuccinimide, for example N-chlorosuccinimide or N-bromosuccinimide, in a solvent such as carbon tetrachloride.

Compounds of formula (II) and (IV), in particular wherein $R^a$ and $R^b$ together with the pyrimidine ring carbon atoms to which they are attached form a fused 5-membered carbocyclic ring, are novel and form a further aspect of the present invention.

The present invention will now be illustrated by the following examples.

EXAMPLES

The structure and purity of the intermediates and examples was confirmed by 1H-NMR and (in nearly all cases) mass spectroscopy, even where not explicitly indicated below.

Intermediate A1—4-(4-Chlorophenyl)benzaldehyde

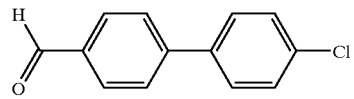

(a) A mixture of 4-formylbenzeneboronic acid (2.50 g, 2 equiv), 4-chloroiodobenzene (1.98 g, 1 equiv), tetrakis (triphenylphosphine)palladium(0) (0.50 g, 0.05 equiv), aqueous sodium carbonate (18 ml, 2M solution, 2 equiv) and dimethoxyethane (50 ml) was stirred at reflux under argon overnight, then cooled and diluted with ethyl acetate. The mixture was filtered as necessary to remove inorganic residues, then the organic layer was washed successively with aqueous citric acid and brine, dried and evaporated. The crude product was purified by chromatography (silica, 5% ethyl acetate in hexane); product fractions were evaporated to a white solid (1.32 g, 72%).

(b) A mixture of 4-chlorobenzeneboronic acid (19.4 g, 1 equiv), 4-bromobenzaldehyde (22.9 g, 1 equiv), palladium (II) acetate (1.4 g, 0.05 equiv) aqueous sodium carbonate (30.3 g in 144 ml solution, 2 equiv) and dimethoxyethane (500 ml) was stirred at reflux under argon for 2.5 h, then evaporated to low volume and diluted with dichloromethane. Workup continued as in (a) above to give identical material (25.2 g, 94%). $^1$H-NMR (CDCl$_3$) δ 10.05 (1H, s), 7.96 (2H, d), 7.73 (2H, d), 7.57 (2H, d), 7.46 (2H, d); MS (AP+) found (M+1)=217, $C_{13}H_9{}^{35}ClO$ requires 216.

Intermediate A2—N-Methyl-4-(4-chlorophenyl) benzylamine

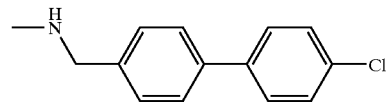

A mixture of Intermediate A1 (3.5 g, 1 equiv), methylamine (32.3 ml of a 2M solution in THF, 4 equiv) and anhydrous magnesium sulphate (4.47 g, 2 equiv) was stirred at room temperature for 16 h, then filtered, the solid washed thoroughly with ethyl acetate, and the combined filtrates evaporated to a white solid (3.7 g). This imine intermediate was suspended in ethanol (100 ml), cooled in ice and sodium borohydride (0.61 g, 1 equiv) added portionwise. The ice bath was removed, and the mixture stirred for 45 min at room temperature then at 50° C. for 1 h. The solvent was removed in vacuo, water was added to the residue, and the product extracted into dichloromethane. Drying and evaporation of the solvent gave a white solid (3.56 g). $^1$H-NMR (CDCl$_3$) δ 7.51 (4H, d), 7.40 (4H, d), 3.79 (2H, s), 2.48 (3H, s); MS (APCI+) found (M+1)=232, $C_{14}H_{14}{}^{35}ClN$ requires 231.

Intermediate A3—N-(2-Diethylaminoethyl)-4-(4-chlorophenyl)benzylamine

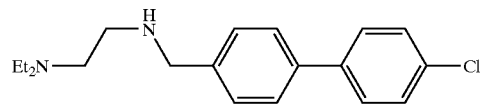

A mixture of Intermediate A1 (55.0 g), N,N-diethylethylenediamine (35.6 ml), 4 A molecular sieve (37 g), and dichloromethane (1100 ml) was reacted at room temperature under argon for 16 h, with occasional agitation. The solid was filtered off and washed with dichloromethane, and the combined filtrates evaporated to a yellow foam (72.4 g). This intermediate imine was reduced with sodium borohydride (8.7 g) in ethanol (850 ml) as described for Intermediate A2, yielding the title compound as a yellow oil (72.7 g). $^1$H-NMR (CDCl$_3$) δ 1.70 (2H, t), 2.22 (6H, s), 2.33 (2H, t), 2.69 (2H, br. m), 3.83 (2H, s), 7.37–7.43 (4H, m), 7.52–7.56 (4H, m).

Intermediate A4—5-Hydroxymethyl-2-(4-trifluoromethylphenyl)pyridine

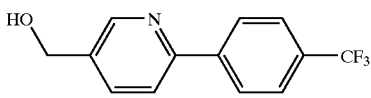

A solution of Intermediate A20 (4.63 g) in dry dichloromethane (100 ml) was cooled to −78° C. under argon, then DIBAL-H (26.7 ml, 1.5M solution in toluene) was added dropwise over 20 min. Stirring was continued for 40 min at −78° C., then 2M hydrochloric acid (52 ml) was added dropwise over 15 min. The solution was allowed to warm slowly to room temperature, then the organic layer was separated, washed with water, dried and evaporated. Chromatography (silica, 1:1 ethyl acetate/hexane) gave the product as a white solid (3.03 g, 75%). $^1$H-NMR (CDCl$_3$) δ 1.85 (1H, t), 4.81 (2H, d), 7.75 (2H, m), 7.83 (1H, dd), 8.11 (1H, d), 8.72 (1H, m); MS (APCI+) found (M+1)=254, C$_{13}$H$_{10}$F$_3$NO requires 253.

Intermediate A5—5-Formyl-2-(4-trifluoromethylphenyl)pyridine

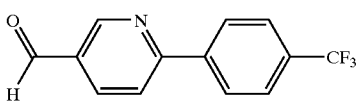

Activated manganese dioxide (3.19 g) was added to a solution of Intermediate A4 (0.75 g) in dichloromethane (50 ml) and stirred at room temperature for 16 h. The solids were filtered off and the filtrate evaporated to a pale yellow solid (0.57 g). $^1$H-NMR (CDCl$_3$) δ 7.7 (2H, d), 7.96 (1H, d), 8.21 (2H, d), 8.27 (1H, dd), 9.17 (1H, d), 10.19 (1H, s); MS (APCI+) found (M+1)=252, C$_{13}$H$_8$F$_3$NO requires 251.

Intermediate A6—Ethyl 2-(4-Chlorophenyl)-4-oxopyrimidine-5-carboxylate

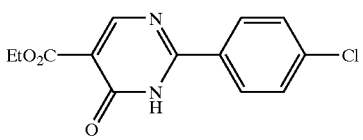

Sodium ethoxide (11.12 ml, 2 equiv) as a 21% w/v solution in ethanol was added dropwise to a suspension of diethyl ethoxymalonate (3.03 ml, 1 equiv) and 4-chlorobenzamidine hydrochloride (4.23 g, 1 equiv) in ethanol (30 ml), then the mixture was heated to reflux for 4 hours. After cooling, the solvent was removed in vacuo and the residue was triturated with ether. The solid was filtered off, then resuspended in water and acidified to pH 2. The product was filtered off, washed with water and dried; yield 2.94 g. $^1$H-NMR (d$_6$-DMSO) δ 1.29 (3H, t), 4.26 (2H, q), 7.65 (2H, m), 8.18 (2H, m), 8.65 (1H, s); MS (APCI−) found (M−1)=277/279; C$_{13}$H$_{11}$ClN$_2$O$_3$ requires 278/280.

Intermediate A7—Ethyl 2-(4-Chlorophenyl)-4-chloropyrimidine-5-carboxylate

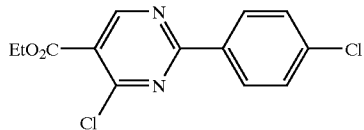

Oxalyl chloride (0.31 ml, 2 equiv) was added to Intermediate A6 (0.49 g) in dichloromethane (20 ml) with ice cooling, then the mixture was stirred for 3 hours with warming to room temperature. Evaporation of the volatile components gave the product as a white solid (2.94 g). $^1$H-NMR (CDCl$_3$) δ 1.44 (3H, t), 4.48 (2H, q), 7.50 (2H, m), 8.45 (2H, m), 9.17 (1H, s); MS (APCI+) found (M+1)=297; C$_{13}$H$_{10}$Cl$_2$N$_2$O$_2$ requires 296.

Intermediate A8—Ethyl 2-(4-Chlorophenyl)pyrimidine-5-carboxylate

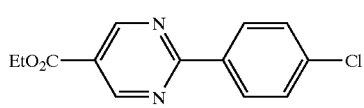

A mixture of Intermediate A7 (6.8 g, 1 equiv), zinc powder (1 .79 g, 1.2 equiv), acetic acid (1.57 ml, 1.2 equiv) and THF (100 ml) was stirred at 60° C. under argon for 18 hours, then a further portion of acetic acid (1 ml) and zinc (1.0 g) was added, and the reaction allowed to continue for a further 24 hours. The solvent was removed in vacuo, the residue was taken up in a mixture of dichloromethane and methanol, and undissolved zinc powder was removed by filtration. After evaporation of the solvent, the product crystallised from ethanol; yield 2.02 g. $^1$H-NMR (CDCl$_3$) δ 1.44 (3H, t), 4.46 (2H, q), 7.48 (2H, m), 8.48 (2H, m), 9.30 (2H, s); MS (APCI+) found (M+1)=263; C$_{13}$H$_{11}$ClN$_2$O$_2$ requires 262.

Intermediate A9—5-Hydroxymethyl-2-(4-trifluoromethylphenyl)pyrimidine

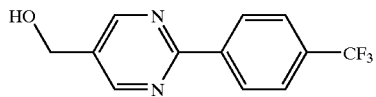

Intermediate A41 (0.96 g) was hydrogenated over 10% palladium on charcoal (96 mg) in a mixture of triethylamine (2 ml) and ethanol (20 ml) for 90 mins at 1 atmosphere pressure. The catalyst was removed by filtration, the solvent was evaporated, and the residue was taken up in ethyl acetate and washed successively with aq. ammonium chloride and aq. sodium bicarbonate. Drying and evaporation gave the title compound (0.77 g). $^1$H-NMR (CDCl$_3$) δ 4.82 (2H, s), 7.75 (2H, m), 8.57 (2H, m), 8.85 (2H, s); MS (APCI+) found (M+1)=255; C$_{12}$H$_9$F$_3$N$_2$O requires 254.

Intermediate A10—3-(4-Trifluoromethylphenoxy)benzyl Alcohol

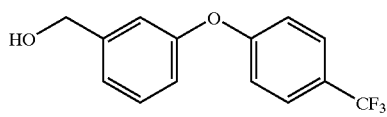

A mixture of 4-chlorobenzotrifluoride (27.1 g, 1.5 equiv), 3-hydroxybenzyl alcohol (12.4 g, 1 equiv), copper (I) chloride (0.2 g, 0.02 equiv), potassium carbonate (8.3 g, 0.6 equiv), 8-quinolinol (0.29 g, 0.02 equiv) and 1,3-dimethyl- 2-imidazolidinone (50 mL) was stirred at 150° C. under argon for 3 days. After cooling, the residue was poured into water and extracted with ethyl acetate. Drying and evaporation, followed by chromatography (silica, dichloromethane) gave the title compound as a pale liquid (11.3 g). $^1$H-NMR (CDCl$_3$) δ 1.88 (1H, t), 4.69 (2H, d), 6.97 (1H, m), 7.04 (3H, m), 7.17 (1H, m), 7.36 (1H, m), 7.57 (2H, m); MS (APCI−) found (M−1)=267; C$_{14}$H$_{11}$F$_3$O$_2$ requires 268.

Intermediate A11—4-(4-Trifluoromethylphenoxy)benzaldehyde

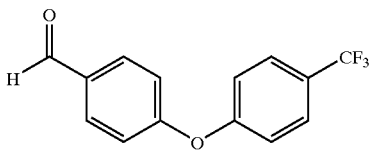

A mixture of 4-(trifluoromethyl)phenol (4.86 g, 1 equiv), 4-fluorobenzaldehyde (3.22 mL, 1 equiv), potassium carbonate (4.15 g, 1 equiv) and dimethylformamide (60 mL) was stirred at 150° C. under argon for 3 hours, then poured into ice/water. The precipitate was filtered off, washed with water, then extracted with hot ethanol. Undissolved solid was removed by filtration, and the filtrate evaporated and purified by chromatography on silica. $^1$H-NMR (CDCl$_3$) δ 7.14 (4H, m), 7.66 (2H, m), 7.90 (2H, m), 9.97 (1H, s); MS (APCI+) found (M+1)=267; C$_{14}$H$_9$F$_3$O$_2$ requires 266.

Intermediate A12—tert-Butyl(2-hydroxyethyl)ethylcarbamate

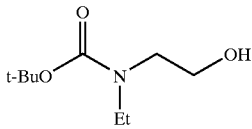

Di-tert-butyl dicarbonate (15.5 g, 1 equiv) was added over a period of 1 hour to a solution of 2-(ethylamino)ethanol (7.5 g 1 equiv) in dichloromethane (30 ml) at 0° C. After stirring at room temperature for 16 hours, the solvent was evaporated and the residue distilled (115° C., 0.6 mmHg) to afford the title compound as a colourless oil (13.42 g). $^1$H-NMR (CDCl$_3$) δ 1.11 (3H, t), 1.47 (9H, s), 3.27 (2H, q), 3.38 (2H, t), 3.75 (2H, t).

Intermediate A13—tert-Butyl[2-(phthalimidyl)ethyl]ethylcarbamate

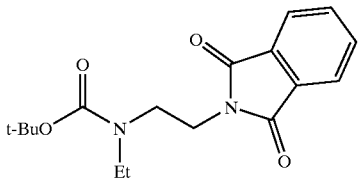

Diethylazodicarbonate (12.35 g, 1 equiv) was added dropwise to a mixture of intermediate A12 (13.42 g, 1 equiv), phthalimide (10.43 g, 1 equiv) and triphenylphosphine (18.6 g, 1 equiv) in THF (200 ml) and the mixture stirred at room temperature for 16 hours. The solvent was evaporated and diethyl ether added. The solution was cooled to 0° C. and the insoluble products removed by filtration. The solvent was evaporated and the residue applied to a column (silica, 9:1 Hexane/ethyl acetate) to afford the title compound as a colourless oil (17 g). $^1$H-NMR (CDCl$_3$) δ 1.13 (3H, m), 1.29 (9H, s), 3.26 (2H, m), 3.48 (2H, m), 3.84 (2H, t), 7.71 (2H, m).

Intermediate A14—tert-Butyl(2-Aminoethyl)ethylcarbamate

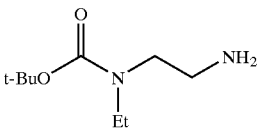

Hydrazine monohydrate (5.2 ml, 2 equiv) was added to a solution of intermediate A13 (17 g, 1 equiv) in ethanol (300 ml) and the reaction stirred for 16 hours at room temperature. The resultant solid was filtered off and the solvent evaporated. The residue was partitioned between diethyl ether and sodium hydroxide (1M, 150 ml) and the organic phase dried (K$_2$CO$_3$) and the solvent removed to afford the title compound as a yellow oil (9.05 g). $^1$H-NMR (CDCl$_3$) δ 1.10 (3H, t), 1.45 (9H, s), 2.65 (2H, q), 2.73 (2H, t), 3.23 (2H, m).

Intermediate A15—3-(4-Trifuoromethyl-biphenyl-4-yl)propan-1-ol

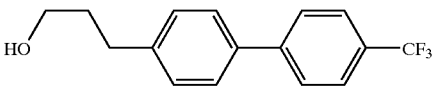

Borane in tetrahydrofuran (1.0M, 44.5 ml, 2.5 equiv) was added dropwise to a solution of intermediate A23 (5.23 g, 1 equiv) in tetrahydrofuran (65 ml) at 0° C. The solution was allowed to warm to room temperature and stirring continued for 16 hours. The reaction was quenched by the addition of water and the mixture extracted with ethyl acetate. The organic phase was washed with aq. sodium bicarbonate, dried (MgSO$_4$) and the solvent evaporated to afford a residue which was applied to a column (silica, dichloromethane) to afford the title compound as a colourless solid (4.31 g). $^1$H-NMR (CDCl$_3$) δ 1.76 (2H, m), 2.67 (2H, t), 3.45 (2H, m), 7.32 (2H, d), 7,64 (2H, d), 7.78 (2H, d), 7.86 (2H, d).

Intermediate A16—3-(4-Trifluoromethyl-biphenyl-4-yl)propionaldehyde

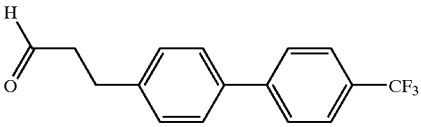

Dimethylsulphoxide (2.36 ml, 2.4 equiv) was added dropwise to a solution of oxalyl chloride (1.46 ml, 1.1 equiv) in dichloromethane (34 ml) at −55° C. and the solution stirred for 2 minutes. A solution of intermediate A15 (4.28 g, 1 equiv) in dichloromethane (40 ml) was added slowly to the solution at −55° C. and the solution stirred for a further 10 minutes prior to the addition of triethylamine (9.7 ml, 5 equiv). After stirring for a further 5 minutes the reaction was allowed to warm to room temperature and then diluted with water. The organic phase was separated, dried (MgSO4) and the solvent removed to afford the title compound (3.48 g). $^1$H-NMR (CDCl$_3$) δ 2.83 (2H, m), 3.02 (2H, t), 7.29 (2H, d), 7.51 (2H, d), 7.67 (4H, s), 9.85 (1H, s). MS (APCI+) found (M+1)=279; C$_{16}$H$_{13}$F$_3$O requires 278.

Intermediate A17—C-(4'-Trifluoromethyl-biphenyl-4-yl)methylamine

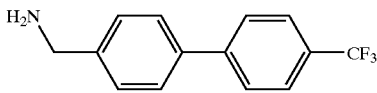

A solution of intermediate A130 (31 g, 1 equiv) in tetrahydrofuran (300 ml) was added dropwise to a solution of lithium aluminium hydride (1.0M in tetrahydrofuran, 188 ml, 1.5 equiv) at room temperature with stirring. The reaction was stirred for 8 hours, after which time aq. ammonium chloride (200 ml) and then water (200 ml) was added. The resultant mixture was filtered through celite and then extracted with dichloromethane. The organic phase was dried (MgSO4) and solvent removed to afford the title compound (26.7 g). $^1$H-NMR (DMSO) δ 3.89 (2H, s), 7.52 (2H, d), 7.73 (2H, d), 7.82 (2H, d), 7.98 (2H, d).

Intermediate A18—N-(1-Ethyl-piperidin-4-yl)-(4'-trifluoromethylphenyl)benzylamine

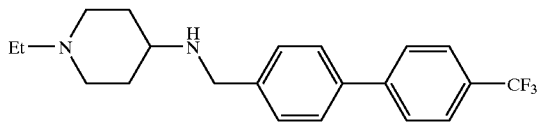

A solution of intermediate A17 (9.3 g, 1 equiv) and 1-ethyl4-piperidone (5.0 ml, 1.05 equiv) in 1,2-dichloroethane (135 ml) was treated with sodium triacetoxyborohydride (11 g, 1.4 equiv) and acetic acid (2.23 g, 1.05 equiv) at room temperature and the mixture was stirred for 24 hours. The reaction was quenched by the addition of sodium hydroxide (2M, 125 ml) and extracted with diethyl ether. The organic phase was dried (MgSO$_4$) and solvent evaporated to afford a residue, which was trituated with hexane to afford the title compound as a off white solid (8.2 g). $^1$H-NMR (CDCl$_3$) δ 1.06 (3H, t), 1.48 (3H, m), 2.01 (4H, m), 2.38 (2H, q), 2.55 (1H, m), 2.92 (2H, m), 3.88 (2H, s), 7.43 (2H, d), 7.59 (2H, d), 7.68 (4H, s).

Intermediate A120—tert-Butyl(2-Amino-2-methylpropyl)-carbamate

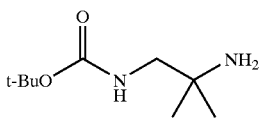

Di-tert-butyl dicarbonate (6.58 g, 1 equiv) in tetrahydrofuran (100 ml) was added dropwise to a solution of 1,2-diamino-2-methylpropane (8.86 g, 3.3 equiv) in tetrahydrofuran (100 ml) at 0° C. The solution was then stirred at room temperature for 16 hours. The solvent was evaporated and the residue partitioned between aq. sodium chloride and ethyl acetate. The organic phase was dried (K$_2$CO3) and solvent evaporated to afford the title compound as a colourless solid (5.45 g). $^1$H-NMR (CDCl$_3$) δ 1.09 (6H, s), 1.45 (9H, s), 3.00 (2H, d). MS (APCI+) found (M+1)=189; C$_9$H$_{20}$N$_2$O requires 188.

Intermediate A121—tert-Butyl(2-Ethylamino-2-methylpropyl)-carbamate

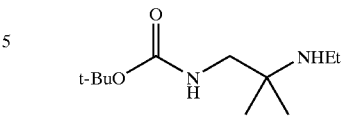

Intermediate A120 (5.45 g, 1 equiv), iodoethane (2.32 ml, 1 equiv) and potassium carbonate (4 g, 1 equiv) in dimethylformamide (80 ml) were stirred at room temperature for 16 hours. Solvent was evaporated and the residue partitioned between dichloromethane and water. The organic layer was dried (K$_2$CO3), solvent evaporated and the residue applied to a column (silica, 10:1 dichloromethane/methanol) to afford the title compound as a light brown oil (3.89 g). $^1$H-NMR (CDCl$_3$) δ 1.05 (6H, s), 1.08 (3H, t), 1.45 (9H, s), 2.54 (2H, q), 3.03 (2H, m). MS (APCI+) found (M+1)=217; C$_{11}$H$_{24}$N$_2$O$_2$ requires 216.

Intermediate A122—N$^2$-Ethyl-2-methylpropane-1,2-diamine dihydrochloride

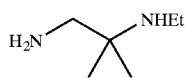

Hydrogen chloride (4M in dioxan, 70 ml) was added to a solution of intermediate A121 (3.89 g) in dioxan (100 ml) and the resulting suspension stirred at room temperature for 16 hours. Solvent was evaporated and the residue suspended in diethyl ether, the resulting solid was filtered off and collected to afford the title compound as a colourless solid (2.99 g). $^1$H-NMR (d$_6$-DMSO) δ 1.26 (3H, t), 1.39 (6H, s), 2.97 (2H, q), 3.19 (2H, s). MS (APCI+) found (M+1)=117; C$_6$H$_{16}$N$_2$ requires 116.

Intermediate A123—2-(2-tert-Butylaminoethyl)phthalimide

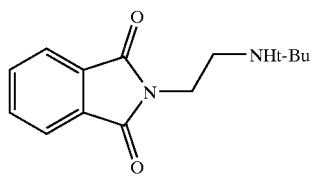

A mixture of 2-bromoethyl phthalimide (20 g, 2 equiv), tert-butylamine (41 ml, 1 equiv) and potassium carbonate (10.86 g, 2 equiv) in dimethylformamide (200 ml) was heated to 50° C. for 48 hours. Solvent was evaporated and the residue partitioned between dichloromethane and water. The organic phase was dried (K$_2$CO$_3$) and solvent removed to afford the title compound as an orange solid (18.93 g). $^1$H-NMR (CDCl$_3$) δ 1.05 (9H, s), 2.85 (2H, t), 3.77 (2H, t), 7.72 (2H, m), 7.85 (2H, m).

Intermediate A124—N-tert-Butylethane-1,2-diamine

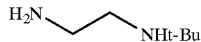

A mixture of intermediate A123 (4 g, 1 equiv) and hydrazine hydrate (1.58 ml, 2 equiv) in methylated spirit (100 ml) was heated to reflux for 16 hours. Solid filtered off and solution used directly in the next step.

The following intermediates were made by the method of Intermediate A1:

| No. | Precursors | Name |
|---|---|---|
| A20 | methyl 6-chloronicotinate, 4-trifluoromethylbenzeneboronic acid | Methyl 6-(4-trifluoromethylphenyl)nicotinate |
| A21 | 4-bromobenzaldehyde, 4-trifluoromethylbenzeneboronic acid | 4-(4-Trifluoromethylphenyl)benzaldehyde |
| A22 | 4-bromoacetophenone, 4-chlorobenzeneboronic acid | 4-acetyl-4'-chlorobiphenyl |
| A23 | 4-(trifluoromethyl)bromobenzene 4-(2-carboxyethyl)phenylboronic acid | 3-(4-Trifluoromethylbiphenyl-4-yl)propionic acid |
| A24 | 2-(4-bromophenoxy)ethanol 4-trifluoromethylbenzeneboronic acid | 2-(4-trifluoromethyl-biphenyloxy)ethanol |
| A130 | 4-bromobenzonitrile 4-trifluoromethylbenzeneboronic acid | 4'-trifluoromethyl-biphenyl-4-carbonitrile |

The following intermediates were made by the method of Intermediate A2:

| No. | Precursor | Structure | Name |
|---|---|---|---|
| A25 | Int. A21 | 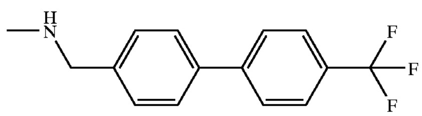 | N-Methyl-4-(4-trifluoromethylphenyl)benzylamine |
| A26 | Int. A5 | 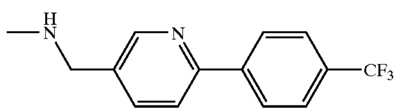 | N-methyl-2-(4-trifluoromethylphenyl)pyrid-5-yl-methylamine |

The following intermediates were made by the method of Intermediate A3:

| No. | Precursor | Structure | Name |
|---|---|---|---|
| A30 | Int. A21 | 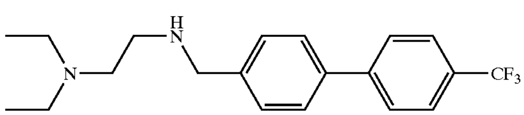 | N-(2-(diethylamino)ethyl)-4-(4-trifluoromethylphenyl)-benzylamine |
| A31 | Int. A5 | 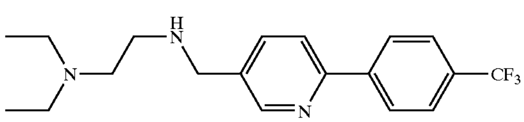 | N-(2-(diethylamino)ethyl)-2-(4-trifluoromethylphenyl)-pyrid-5-ylmethylamine |
| A32 | Int. A50 | 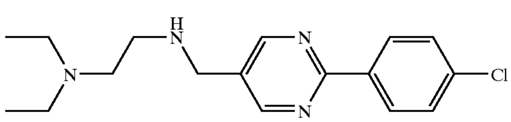 | N-(2-(diethylamino)ethyl-2-(4-chlorophenyl)pyrimid-5-ylmethylamine |
| A33 | Int. A51 | 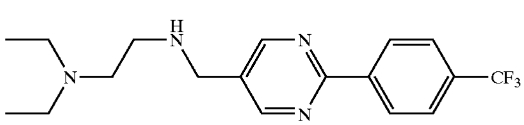 | N-(2-(diethylamino)ethyl)-2-(4-trifluoromethylphenyl)-pyrimid-5-ylmethylamine |
| A34 | Int. A21 | 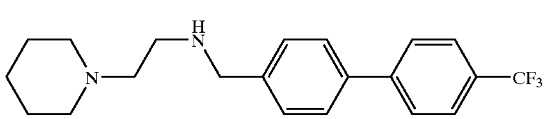 | N-(2-(1-piperidino)ethyl)-4-(4-trifluoromethylphenyl)-benzylamine |

-continued

| No. | Precursor | Structure | Name |
|---|---|---|---|
| A35 | Int. A22 | 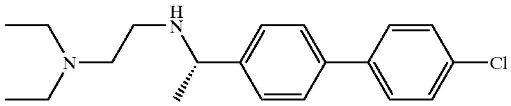 | (±)-N-(2-(diethylamino)ethyl)-1-(4-(4-chlorophenyl)-phenyl)ethylamine |
| A36 | Int. A54 | 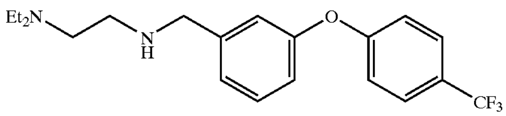 | N-(2-(diethylamino)ethyl)-3-(4-trifluoromethylphenoxy)-benzylamine |
| A37 | Int. A11 | 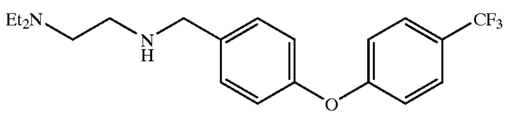 | N-(2-(diethylamino)ethyl)-4-(4-trifluoromethylphenoxy)-benzylamine |
| A38 | Int. A14<br>Int. A21 | 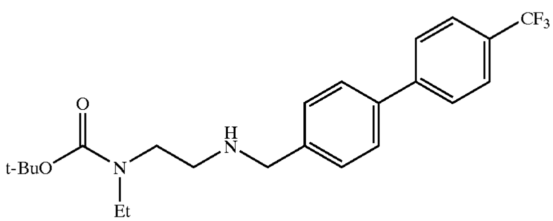 | tert-Butyl {2-[4-(4-trifluoromethylphenyl)benzylamino]-ethyl}ethylcarbamate |
| A39 | Int. A16 | 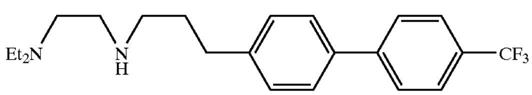 | N-(2-(diethylamino)ethyl)-3-(4-trifluoromethylbiphenyl-4-yl)propylamine |
| A140 | Int. A55 | 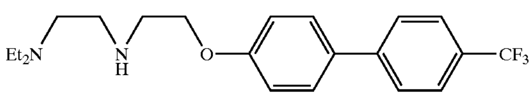 | N-(2-(diethylamino)ethyl)-2-(4-trifluoromethylbiphenyl-4-yloxy)ethylamine |
| A141 | Int. A21<br>Int. A122 | 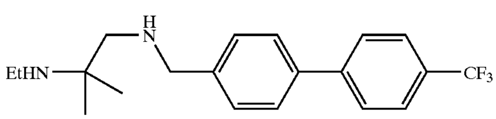 | N-[(2-(diethylamino)-2-ethyl)propyl]-4-(4-trifluoromethyl-phenyl)benzylamine |
| A142 | Int. A21<br>Int. A124 | 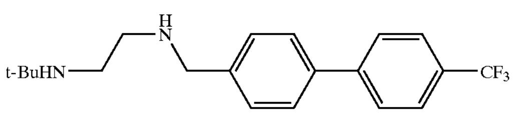 | N-tert-Butylaminoethyl-4-(4-trifluoromethylphenyl)-benzylamine |

The following intermediates were made by the method of Intermediate A4:

| No. | Precursor | Name |
|---|---|---|
| A40 | Int. A8 | 5-Hydroxymethyl-2-(4-chlorophenyl)pyrimidine |
| A41 | Int. A53 | 4-chloro-5-hydroxymethyl-2-(4-trifluoromethylphenyl)pyrimidine |

The following intermediates were made by the method of Intermediate A5:

| No. | Precursor | Name |
|---|---|---|
| A50 | Int. A40 | 5-Formyl-2-(4-chlorophenyl)pyrimidine |
| A51 | Int. A9 | 5-Formyl-2-(4-trifluoromethylphenyl)pyrimidine |
| A54 | Int. A10 | 3-(4-trifluoromethylphenoxy)benzaldehyde |

The following intermediate was made by the method of Intermediate A6:

| No. | Precursors | Name |
|---|---|---|
| A52 | diethyl ethoxymalonate, 4-trifluoromethyl-benzamidine.HCl | Ethyl 2-(4-trifluoromethylphenyl)-4-oxopyrimidine-5-carboxylate |

The following intermediate was made by the method of Intermediate A7:

| No. | Precursor | Name |
|---|---|---|
| A53 | Int. A52 | Ethyl 2-(4-trifluoromethylphenyl)-4-chloropyrimidine-5-carboxylate |

The following intermediate was made by the method of Intermediate A16:

| No. | Precursor | Name |
|---|---|---|
| A55 | Int. A24 | (4-trifluoromethylbiphenyl-4-yloxy)acetaldehyde |

The following intermediates were made by the method of Intermediate A18, using Intermediate A17 and the appropriately substituted 1-alkyl-4-piperidone:

| No. | Name |
|---|---|
| A60 | N-(1-methylpiperidin-4-yl)-(4'-trifluoromethylphenyl)benzylamine |
| A61 | N-(1-isopropylpiperidin-4-yl)-(4'-trifluoromethylphenyl)benzylamine |
| A62 | N-(1-(2-methoxyethyl)piperidin-4-yl)-(4'-trifluoromethylphenyl)benzylamine |

The following compounds are commercially available:
Intermediate B1, 2-thiouracil; Intermediate B2, 5-methyl-2-thiouracil; Intermediate B3, 5-ethyl-2-thiouracil; Intermediate B4, 5-propyl-2-thiouracil; Intermediate B5, 5,6-dimethyl-2-thiouracil;

The following compounds are available by literature methods:
Intermediate B6, 5-carbethoxy-2-thiouracil (J. Amer. Chem. Soc. 794, 64 (1942));
Intermediate B7, 5,6-trimethylene-2-thiouracil (J. Amer. Chem. Soc. 3108, 81 (1959));
Intermediate B8, 5,6-tetramethylene-2-thiouracil (J. Org. Chem. 133, 18 (1953));
Intermediate B9, 5-methoxy-2-thiouracil (J. Chem. Soc. 4590 (1960)).
Intermediate B10—5-(2-Hydroxyethyl)-2-thiouracil A solution of ethyl formate (33.1 ml, 2.1 equiv) and γ-butyrolactone (15 ml, 1 equiv) in ether (400 ml) was added dropwise with stirring to a solution of potassium t-butoxide (52.5 g, 2.4 equiv) in tetrahydrofuran (400 ml). The mixture was allowed to warm to room temperature, and stirred overnight. The solvent was removed in vacuo, 2-propanol (600 ml) and thiourea (29.7 g, 2 equiv) were added, and the mixture was heated to reflux for 5 h. After cooling to room temperature, the precipitate was filtered off, dissolved in water (500 ml), and washed twice with ether. The aqueous solution was acidified to pH5.5 with acetic acid, and the resulting precipitate was filtered off, washed thoroughly with water, and dried in vacuo; yield 23.85 g. $^1$H-NMR ($d_6$-DMSO) δ 2.36 (2H, t), 3.47 (2H, m), 4.57 (1H, m), 7.24 (1H, s), 12.2 & 12.4 (each 1H, br s); MS (APCI−) found (M−H)=171; $C_6H_8N_2O_2S$ requires 172.

Intermediate B111—Ethyl(2,4-dioxo-4H-benzo[d][1,3]oxazin-1-yl)acetate

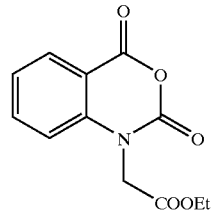

Isatoic anhydride (10 g, 1 equiv) in dimethylformamide (30 ml) was added dropwise to a suspension of sodium hydride (2.45 g, 60% in mineral oil, 1 equiv) in dimethylformamide (70 ml) at room temperature. The reaction was stirred for 1 hour prior to the addition of ethyl bromoacetate (6.8 ml, 1 equiv) and the resulting mixture stirred for 16 hours. Solvent evaporated, the residue suspended in water and the solid collected. The title compound was obtained by crystallisation from ethyl acetate (10.5 g). $^1$H-NMR (CDCl$_3$) δ 1.29 (3H, t), 4.27 (2H, q), 4.82 (2H, s), 6.96 (1H, d), 7.33 (1H, t), 7.74 (1H, dt), 8.19 (1H, dd).

Intermediate B112—Ethyl(4-oxo-2-thioxo-3,4-dihydro-2H-quinazolin-1-yl)acetate

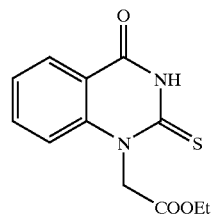

Intermediate B111 (2.64 g, 1 equiv) and thiourea (2.42 g, 4 equiv) in 1-methyl-2-pyrrolidinone (40 ml) was heated to 180° C. for 2 hours. After cooling the mixture was treated with water and the resultant solid collected by filtration. This solid was applied to a column (silica, 2% methanol/dichloromethane) to afford the title compound as a colourless solid (0.169 g). $^1$H-NMR (CDCl$_3$) δ 1.22 (3H, t), 4.21 (2H, q), 5.53 (2H,br s), 7.46 (1H, t), 7.53 (1H, d), 7.81 (1H, dt), 8.07 (1H, dd).

Intermediate B113—Methyl 3-[3-(1-Phenylmethanoyl)thioureido]thiophene-2-carboxylate

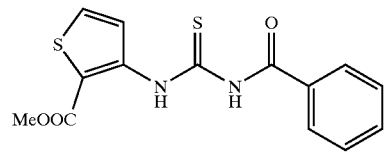

Methyl-3-amino-2-thiophene carboxylate (30 g, 1 equiv) and benzoyl isothiocyanate (46 ml, 1.8 equiv) in acetone (250 ml) were heated to 65° C. for 30 minutes. After cooling the solution was concentrated and the resulting solid filtered off and dried (40.54 g). $^1$H-NMR (CDCl$_3$) δ 3.98 (3H, s), 7.54 (4H, m), 7.94 (2H, m), 8.81 (1H, d), 9.15 (1H,br s); MS (APCI+) found (M+1)=321; $C_{14}H_{12}N_2O_3S_2$ requires 320.

Intermediate B114—2-Thioxo-2,3-dihydro-1H-thieno[3,2-d]pyrimidin-4-one

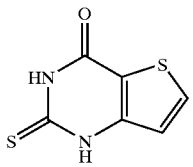

Potassium hydroxide (13.83 g, 2 equiv) was dissolved in ethanol (1000 ml) and then poured onto intermediate B113 (40.54 g, 1 equiv) with stirring. The mixture was heated to reflux for 1 hour and after cooling the title compound was obtained by filtration (17.32 g). $^1$H-NMR (CDCl$_3$) δ 6.87 (1H, d), 7.77 (1H, d), 10.46 (2H, br s); MS (APCI−) found (M−1)=183; $C_6H_4N_2OS_2$ requires 184.

The following intermediates were prepared by the method of Intermediate B10

| No. | Precursor | Name |
|---|---|---|
| B11 | monoethyl succinate | 5-carboxymethyl-2-thiouracil |
| B12 | ethyl ethoxyacetate | 5-ethoxy-2-thiouracil |
| B13 | ethyl (methylthio)acetate | 5-methylthio-2-thiouracil |

Intermediate B20—2-(4-Fluorobenzylthio)-5-methylpyrimidin-4-one

A mixture of Intermediate B2 (9.45 g, 1 equiv), 4-fluorobenzyl chloride (7.96 ml, 1 equiv), potassium carbonate (18.4 g, 2 equiv) and dimethyl formamide (100 ml) was stirred at 90° C. under argon for 16 h. The DMF was removed in vacuo, water was added, and the product was extracted into ethyl acetate. The organic layer was dried and evaporated, and the residue was triturated with petroleum ether to obtain the title compound as a white solid (8.76 g). $^1$H-NMR (CDCl$_3$) δ 2.02 (3H, s), 4.38 (2H, s), 6.97 (2H, m), 7.35 (2H, m), 7.74 (1H, s); MS (APCI+) found (M+1)=251; $C_{12}H_{11}FN_2OS$ requires 250.

The following intermediates were prepared by the method of Intermediate B20:

| No. | Precursor | Name |
|---|---|---|
| B21 | Int. B1 | 2-(4-fluorobenzylthio)pyrimidin-4-one |
| B22 | Int. B3 | 2-(4-fluorobenzylthio)-5-ethylpyrimidin-4-one |
| B23 | Int. B4 | 2-(4-fluorobenzylthio)-5-propylpyrimidin-4-one |
| B24 | Int. B6 | 2-(4-fluorobenzylthio)-5-ethoxycarbonylpyrimidin-4-one |
| B25 | Int. B10 | 2-(4-fluorobenzylthio)-5-(2-hydroxyethyl)pyrimidin-4-one |
| B26 | Int. B5 | 2-(4-fluorobenzylthio)-5,6-dimethylpyrimidin-4-one |
| B27 | Int. B7 | 2-(4-fluorobenzylthio)-5,6-trimethylenepyrimidin-4-one |
| B28 | Int. B8 | 2-(4-fluorobenzylthio)-5,6-tetramethylenepyrimidin-4-one |
| B29 | Int. B9 | 2-(4-fluorobenzylthio)-5-methoxypyrimidin-4-one |
| B30 | Int. B12 | 2-(4-fluorobenzylthio)-5-ethoxy-pyrimidin-4-one |
| B31 | Int. B13 | 2-(4-fluorobenzylthio)-5-methylthiopyrimidin-4-one |
| B132 | Int. B114 | 2-(4-fluorobenzylthio)-1H-thieno[3,2-d]pyrimidin-4-one |

The following intermediates were prepared by the method of Intermediate B20 and the appropriate benzyl chloride.

| No. | Precursor | Name |
|---|---|---|
| B133 | Int. B7<br>2,3-difluorobenzyl chloride | 2-(2,3-difluorobenzylthio)-5,6-trimethylenepyrimidin-4-one |
| B134 | Int. B7<br>3,4-difluorobenzyl chloride | 2-(3,4-difluorobenzylthio)-5,6-trimethylenepyrimidin-4-one |
| B135 | Int. B7<br>2,3,4-trifluorobenzyl chloride | 2-(2,3,4-trifluorobenzylthio)-5,6-trimethylenepyrimidin-4-one |
| B136 | Int. B7<br>2-fluorobenzyl chloride | 2-(2-fluorobenzylthio)-5,6-trimethylenepyrimidin-4-one |

Intermediate B37—2-(4-Fluorobenzylthio)-5-hydroxymethylpyrimidin-4-one

Borane-tetrahydrofuran complex (143 ml, 2.2 equiv, 1.0M in THF) was added dropwise to an ice-cooled solution of Intermediate B24 (20 g, 1 equiv) in dry THF (700 ml) under argon with stirring. After a further 30 min at 0° C., the mixture was allowed to warm to room temperature and stirring continued overnight. The solvent was evaporated, 50% aqueous acetic acid (500 ml) was added with stirring, and the mixture was evaporated to dryness. The residue was digested with hot water (500 ml) for 5 min, then the solid was filtered off. Both this solid and the filtrate were extracted with dichloromethane, and the organic extracts were combined and purified by chromatography (silica, 2–8% methanol in dichloromethane). Product fractions were evaporated to a white solid (6.14 g). $^1$H-NMR (d$_6$-DMSO) δ 4.25 (2H,S), 4.39 (2H, S), 7.14 (2H, t), 7.45 (2H, m), 7.82 (1H, br s); MS (APCI+) found (M+1)=267; $C_{12}H_{11}FN_2O_2S$ requires 266.

Intermediate B38—2-(4-Fluorobenzylthio)-5-isopropoxycarbonylmethylpyrimidin-4-one A mixture of Intermediate B11 (2.60 g, 1 equiv), 4-fluorobenzyl bromide (1.74 ml, 1 equiv) and 2-propanol (50 ml) was stirred at reflux for 3 h, then concentrated to a slurry in vacuo and diluted with ether. The solid was filtered off, washed with ether and dried; yield 2.87 g. $^1$H-NMR (d$_6$-DMSO) δ 1.17 (6H, d), 3.31 (2H, s), 4.40 (2H, s), 4.89 (1H, m), 7.14 (2H, t), 7.45 (2H, m), 7.84 (1H, s); MS (APCI+) found (M+1)=325; $C_{15}H_{17}FN_2O_3S$ requires 324.

Intermediate B40—1-(tert-Butoxycarbonylmethyl)-2-(4-fluorobenzylthio)-5-methyl-pyrimidin-4-one A mixture of Intermediate B20 (6.30 g, 1 equiv), t-butyl iodoacetate (6.1 g, 1 equiv), diisopropylethylamine (5.27 ml, 1.2 equiv) and dichloromethane (100 ml) was stirred at ambient temperature under argon for 16 h, then the solution was washed with aq. ammonium chloride and aq. sodium bicarbonate, dried and evaporated. Chromatography (silica, ethyl acetate+0.5% v/v aq. ammonia) followed by crystallisation from ethyl acetate gave the title compound as a white solid (3.36 g). $^1$H-NMR (CDCl$_3$) δ 1.44 (9H, s), 2.01 (3H, d), 4.36 (2H, s), 4.51 (2H, s), 6.98 (3H, m), 7.36 (2H, m); MS (APCI+) found (M+1)=365; $C_{18}H_{21}FN_2O_3S$ requires 364.

The following intermediates were prepared by the method of Intermediate B40:

| No. | Precursor | Name |
|---|---|---|
| B41 | Int. B21 | 1-(tert-Butoxycarbonylmethyl)-2-(4-fluorobenzylthio)pyrimidin-4-one |
| B42 | Int. B22 | 1-(tert-Butoxycarbonylmethyl)-2-(4-fluorobenzylthio)-5-ethylpyrimidin-4-one |

-continued

| No. | Precursor | Name |
|---|---|---|
| B43 | Int. B23 | 1-(tert-Butoxycarbonylmethyl)-2-(4-fluorobenzylthio)-5-propylpyrimidin-4-one |
| B44 | Int. B24 | 1-(tert-Butoxycarbonylmethyl)-2-(4-fluorobenzylthio)-5-ethoxycarbonyl-pyrimidin-4-one |
| B45 | Int. B38 | 1-(tert-Butoxycarbonylmethyl)-2-(4-fluorobenzylthio)-5-isopropoxycarbonylmethylpyrimidin-4-one |
| B46 | Int. B37 | 1-(tert-Butoxycarbonylmethyl)-2-(4-fluorobenzylthio)-5-hydroxymethyl-pyrimidin-4-one |
| B47 | Int. B25 | 1-(tert-Butoxycarbonylmethyl)-2-(4-fluorobenzylthio)-5-(2-hydroxyethyl)-pyrimidin-4-one |
| B48 | Int. B26 | 1-(tert-Butoxycarbonylmethyl)-2-(4-fluorobenzylthio)-5,6-dimethyl-pyrimidin-4-one |
| B49 | Int. B27 | 1-(tert-Butoxycarbonylmethyl)-2-(4-fluorobenzylthio)-5,6-trimethylene-pyrimidin-4-one |
| B50 | Int. B28 | 1-(tert-Butoxycarbonylmethyl)-2-(4-fluorobenzylthio)-5,6-tetramethylene-pyrimidin-4-one |
| B51 | Int. B29 | 1-(tert-Butoxycarbonylmethyl)-2-(4-fluorobenzylthio)-5-methoxy-pyrimidin-4-one |
| B52 | Int. B30 | 1-(tert-Butoxycarbonylmethyl)-2-(4-fluorobenzylthio)-5-ethoxypyrimidin-4-one |
| B53 | Int. B31 | 1-(tert-Butoxycarbonylmethyl)-2-(4-fluorobenzylthio)-5-methylthio-pyrimidin-4-one |
| B154 | Int. B133 | 1-(tert-Butoxycarbonylmethyl)-2-(2,3-difluorobenzylthio)-5,6-tetramethylenepyrimidin-4-one |
| B155 | Int. B134 | 1-(tert-Butoxycarbonylmethyl)-2-(3,4-difluorobenzylthio)-5,6-tetramethylenepyrimidin-4-one |
| B156 | Int. B135 | 1-(tert-Butoxycarbonylmethyl)-2-(2,3,4-trifluorobenzylthio)-5,6-tetramethylenepyrimidin-4-one |
| B157 | Int. B136 | 1-(tert-Butoxycarbonylmethyl)-2-(2-fluorobenzylthio)-5,6-tetramethylene-pyrimidin-4-one |
| B158 | Int. B132 | 1-tert-Butoxycarbonylmethyl)-2-(4-fluorobenzylthio)-4-oxo-4H-thieno[3,2-d]pyrimidin-1-one |

The following intermediate was prepared by the method of Intermediate B20:

| No. | Precursor | Name |
|---|---|---|
| B159 | B112 | Ethyl [2-(4-fluorobenzylthio)-4-oxo-4H-quinazolin-1-yl]acetate |

Intermediate B56—1-(tert-Butoxycarbonylmethyl)-2-(4-fluorobenzylthio)-5-chloro-pyrimidin-4-one A mixture of Intermediate B41 (7.45 g, 1 equiv), N-chlorosuccinimide (2.84 g, 1 equiv) and carbon tetrachloride (150 ml) was stirred at reflux under argon for 2 h, then the solution was evaporated. Chromatography (silica, ethyl acetate) followed by trituration with ether gave the title compound as a white solid (4.45 g). $^1$H-NMR (CDCl$_3$) δ 1.45 (9H, s), 4.40 (2H, s), 4.50 (2H, s), 6.99 (2H, m), 7.35 (2H, m), 7.40 (1H, s); MS (APCI+) found (M+1)=385/387; $C_{17}H_{18}ClFN_2O_3S$ requires 384/386.

Intermediate B57—1-(tert-Butoxycarbonylmethyl)-2-(4-fluorobenzylthio)-5-bromo-pyrimidin-4-one Prepared as Intermediate B56, but using N-bromosuccinimide in place of N-chlorosuccinimide. $^1$H-NMR (CDCl$_3$) δ 1.45 (9H, s), 4.40 (2H, s), 4.49 (2H, s), 6.99 (2H, m), 7.35 (2H, m), 7.53 (1H, s); MS (APCI+) found (M+1)=429/431; $C_{17}H_{18}BrFN_2O_3S$ requires 428/430.

Intermediate B58—1-(tert-Butoxycarbonylmethyl)-2-(4-fluorobenzylthio)-5-methylsulfinylpyrimidin-4-one m-Chloroperbenzoic acid (0.93 g) was added to an ice-cooled slurry of Intermediate B53 (1.50 g) in dichloromethane (20 ml). The resulting solution was allowed to warm to room temperature and stirred for 30 min, then washed with aq. sodium bicarbonate. Chromatography (silica, 3–8% methanol in ethyl acetate) gave the title compound as a white solid (1.15 g). $^1$H-NMR (CDCl$_3$) δ 1.46 (9H, s), 2.94 (3H, s), 4.51 (4H, m), 7.01 (2H, m), 7.37 (2H, m), 7.60 (1H, s); MS (APCI+)found (M+1)=413; $C_{18}H_{21}FN_2O_4S_2$ requires 412.

Intermediate B60—1-(Carboxymethyl)-2-(4-fluorobenzylthio)-5-methylpyrimidin-4-one

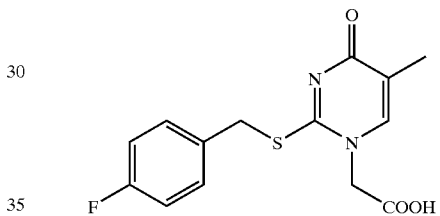

Intermediate B40 (3.88 g) was added to solution of trifluoroacetic acid (10 ml) in dichloromethane (20 ml) under argon, and stirred overnight at room temperature. Evaporation of the solvent and trituration with ether gave the title compound as a white solid (3.04 g). $^1$H-NMR (d$_6$-DMSO) δ 1.81 (3H, d), 4.42 (2H, s), 4.66 (2H, s), 7.14 (2H, m), 7.47 (2H, m), 7.63 (1H, m); MS (APCI+)found (M+1)=309; $C_{14}H_{13}FN_2O_3S$ requires 308.

The following intermediates were prepared by the method of Intermediate B60:

| No. | Precursor | Structure | Name |
|---|---|---|---|
| B61 | Int. B41 | 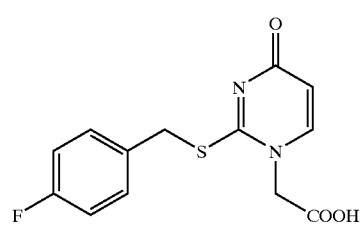 | 1-(Carboxymethyl)-2-(4-fluorobenzylthio)pyrimidin-4-one |

-continued

| No. | Precursor | Structure | Name |
|---|---|---|---|
| B62 | Int. B42 | 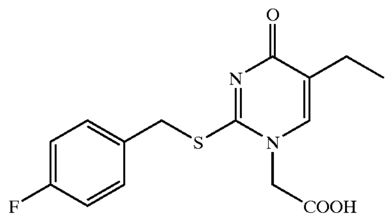 | 1-(Carboxymethyl)-2-(4-fluorobenzylthio)-5-ethylpyrimidin-4-one |
| B63 | Int. B43 | 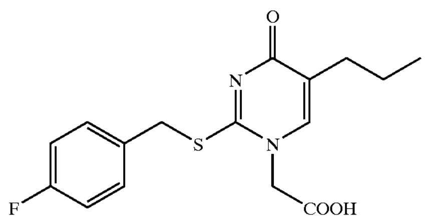 | 1-(Carboxymethyl)-2-(4-fluorobenzylthio)-5-propylpyrimidin-4-one |
| B64 | Int. B44 | 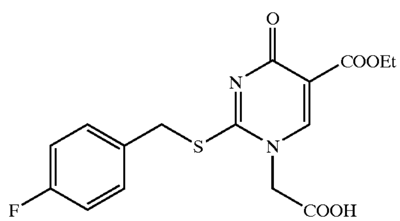 | 1-(Carboxymethyl)-2-(4-fluorobenzylthio)-5-ethoxycarbonyl-pyrimidin-4-one |
| B65 | Int. B45 | 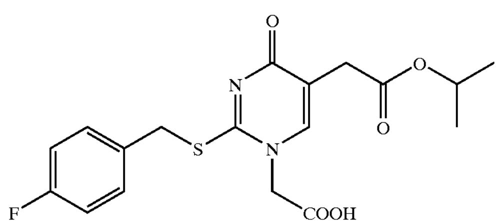 | 1-(Carboxymethyl)-2-(4-fluorobenzylthio)-5-isopropoxycarbonyl-methylpyrimidin-4-one |
| B66 | Int. B46 | 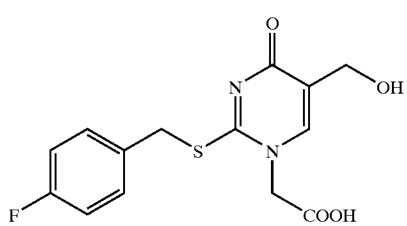 | 1-(Carboxymethyl)-2-(4-fluorobenzylthio)-5-hydroxymethyl-pyrimidin-4-one |
| B67 | Int. B47 | 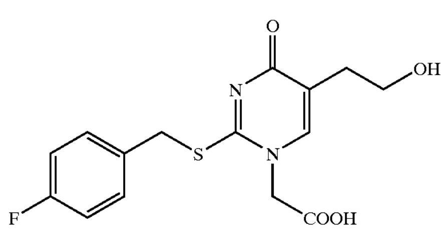 | 1-(Carboxymethyl)-2-(4-fluorobenzylthio)-5-(2-hydroxyethyl)-pyrimidin-4-one |
| B68 | Int. B48 | 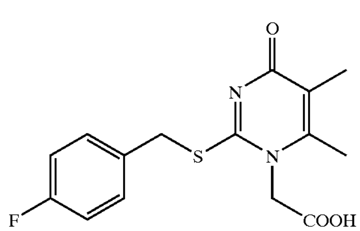 | 1-(Carboxymethyl)-2-(4-fluorobenzylthio)-5,6-dimethylpyrimidin-4-one |

| No. | Precursor | Structure | Name |
|-----|-----------|-----------|------|
| B69 | Int. B49 | 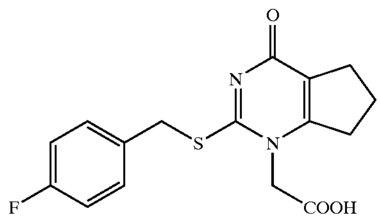 | 1-(Carboxymethyl)-2-(4-fluorobenzylthio)-5,6-trimethylene-pyrimidin-4-one |
| B70 | Int. B50 | 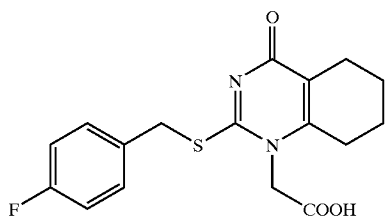 | 1-(Carboxymethyl)-2-(4-fluorobenzylthio)-5,6-tetramethylene-pyrimidin-4-one |
| B71 | Int. B56 | 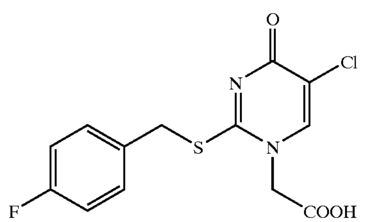 | 1-(Carboxymethyl)-2-(4-fluorobenzylthio)-5-chloropyrimidin-4-one |
| B72 | Int. B57 | 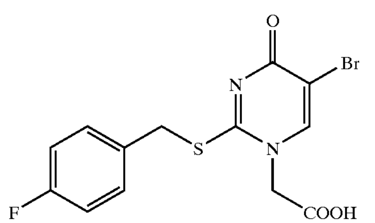 | 1-(Carboxymethyl)-2-(4-fluorobenzylthio)-5-bromopyrimidin-4-one |
| B73 | Int. B51 | 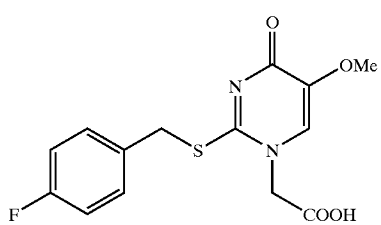 | 1-(Carboxymethyl)-2-(4-fluorobenzylthio)-5-methoxypyrimidin-4-one |
| B74 | Int. B52 | 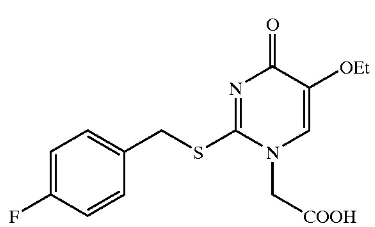 | 1-(Carboxymethyl)-2-(4-fluorobenzylthio)-5-ethoxypyrimidin-4-one |

| No. | Precursor | Structure | Name |
|---|---|---|---|
| B75 | Int. B53 | 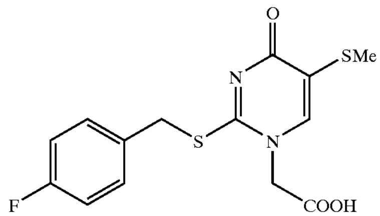 | 1-(Carboxymethyl)-2-(4-fluorobenzylthio)-5-methylthiopyrimidin-4-one |
| B76 | Int. B58 | 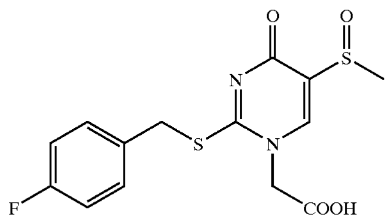 | 1-(Carboxymethyl)-2-(4-fluorobenzylthio)-5-methylsulfinyl-pyrimidin-4-one |
| B177 | Int. B154 | 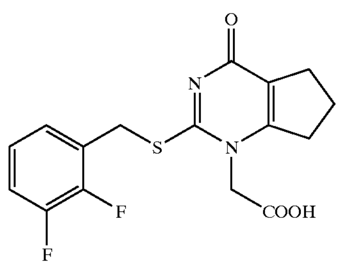 | 1-(Carboxymethyl)-2-(2,3-difluorobenzylthio)-5,6-trimethylene-pyrimidin-4-one |
| B178 | Int. B155 | 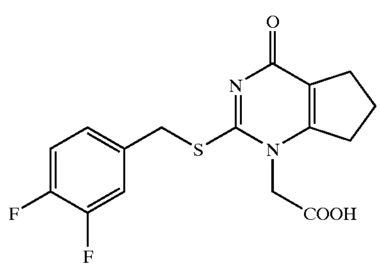 | 1-(Carboxymethyl)-2-(3,4-difluorobenzylthio)-5,6-trimethylene-pyrimidin-4-one |
| B179 | Int. B156 | 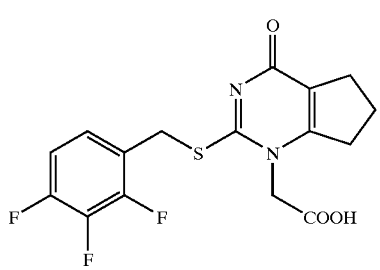 | 1-(Carboxymethyl)-2-(2,3,4-trifluorobenzylthio)-5,6-trimethylene-pyrimidin-4-one |
| B180 | Int. B157 | 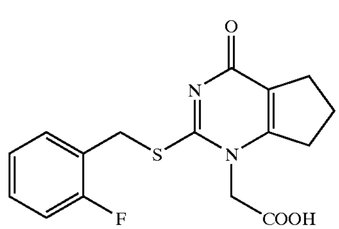 | 1-(Carboxymethyl)-2-(2-fluorobenzylthio)-5,6-trimethylene-pyrimidin-4-one |

-continued

| No. | Precursor | Structure | Name |
|---|---|---|---|
| B181 | Int. B158 | 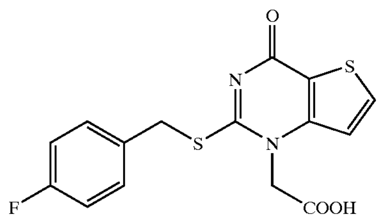 | [2-(4-Fluorobenzylthio)-4-oxo-4H-thieno[3,2-d]pyrimidin-1-yl]-acetic acid |
| B182 | Int. B159 | 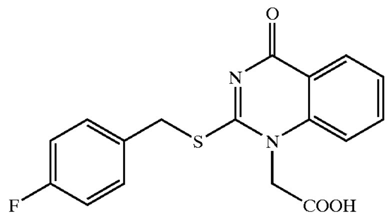 | [2-(4-Fluorobenzylthio)-4-oxo-4H-quinazolin-1-yl]acetic acid |

Intermediate B80—1-(N-Methyl-N-(4-(4-Chlorophenyl)benzyl)aminocarbonylmethyl)-2-(4-fluorobenzyl)thio-5-(2-azidoethyl)pyrimidin-4-one

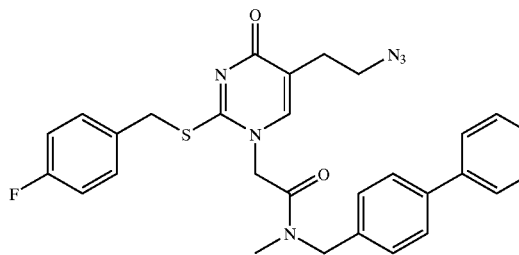

A mixture of Example 39 (1.88 g, 1 equiv), methanesulfonic anhydride (0.713 g, 1.2 equiv), triethylamine (0.665 ml) and dichloromethane (20 ml) was stirred at 0° C. for 4 h. The solution was washed with water, dried and evaporated to a pale foam (2.4 g). This was dissolved in dimethylformamide (20 ml), sodium azide (0.266 g, 1.2 equiv) was added, and the mixture was stirred under argon at room temperature overnight. The solvent was evaporated, the residue was partitioned between water and dichloromethane, and the organic layer was dried and evaporated. Chromatography (silica, ethyl acetate) gave the title compound as a white solid. $^1$H-NMR (CDCl$_3$) δ 2.66 (2H, m), 2.88 (3H, s), 3.60(2H, m), 4.46–4.64 (6H, m), 6.84–750 (12H, m), 8.02 (1H, s); MS (APCI+) found (M+1)=577/579; C$_{29}$H$_{26}$ClFN$_6$O$_2$S requires 576/578.

The following compound was prepared by the method of Intermediate B80

| No. | Precursor | Name |
|---|---|---|
| B81 | Example 42 | 1-(N-(2-(Diethylamino)ethyl)-N-(4-(4-trifluoromethyl-phenyl)benzyl)amino-carbonylmethyl)-2-(4-fluorobenzyl)thio-5-(2-azidoethyl)pyrimidin-4-one |

Example 1—1-(N-(2-(Diethylamino)ethyl)-N-(4-(4-trifluoromethylphenyl)benzyl)aminocarbonylmethyl)-2-(4-fluorobenzyl)thio-5-ethylpyrimidin-4-one bitartrate

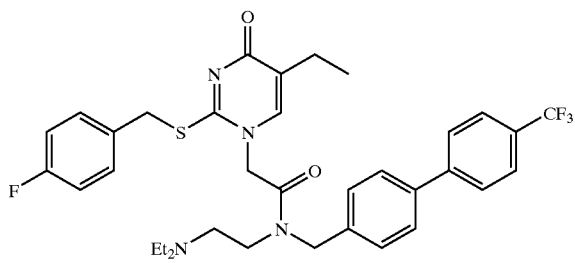

A mixture of Intermediate A30 (0.403 g, 1 equiv), Intermediate B62 (0.371 g, 1 equiv), HATU (0.426 g, 1.2 equiv), di-isopropylethylamine (0.482 ml, 2.4 equiv) and dichloromethane (15 ml) was stirred at room temperature overnight, then washed with aqueous ammonium chloride and aqueous sodium bicarbonate. The organic layer was dried and evaporated, and the product purified by chromatography (silica, 5% methanol in dichloromethane). Product fractions were evaporated to a white foam (0.627 g). This free base (0.612 g) was dissolved in methanol (10 ml), tartaric acid (0.14 g) was added, the mixture was stirred for 5 mins then evaporated. Trituration with ether gave the bitartrate salt as a white solid (0.622 g). $^1$H-NMR (d$_6$-DMSO, ca 1:1 rotamer mixture) δ 0.96 (3H, m), 1.07 (6H, m), 2.27 (2H, m), 2.59 (2H, m), 2.84 (2H, m), 3.37/3.50 (4H, m), 4.26 (2H, s), 4.39/4.43 (2H, 2×s), 4.64/4.72 (2H, 2×s), 4.94/5.09 (2H, 2×s), 7.11/7.14 (2H, 2×m), 7.36–7.49 (5H, m), 7.63/7.72 (2H, 2×d), 7.84 (4H, m); MS (APCI+) found (M+1)=655; C$_{35}$H$_{38}$F$_4$N$_4$O$_2$S requires 654.

Example 2—1-(N-(2-(Diethylamino)ethyl)-N-(2-(4-trifluoromethylphenyl)pyrid-5-yl-methyl) aminocarbonylmethyl)-2-(4-fluorobenzyl)thio-5-ethylpyrimidin-4-one Bitartrate

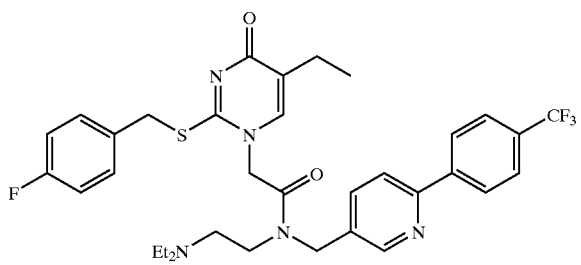

Prepared from intermediates A31 and B62 by the method of Example 1. $^1$H-NMR (d$_6$-DMSO, ca 2:1 rotamer mixture) δ 0.93 (6H, m), 1.08 (3H, m), 2.27 (2H, m), 2.66 (4H, m), 3.39/3.45 (4H, m), 4.21 (2H, s), 4.39/4.42 (2H, 2×s), 4.66/4.77 (2H, 2×s), 4.97/5.10 (2H, 2×s), 7.09/7.12 (2H, 2×t), 7.42/7.49 (2H, 2×t), 7.79/7.86 (1H, 2×dd), 7.87 (2H, d), 7.97/8.06 (1H, 2×dd), 8.28 (2H, d), 8.62/8.71 (2H, 2×s); MS (APCI+) found (M+1)=656; C$_{34}$H$_{37}$F$_4$N$_5$O$_2$S requires 655.

Example 3(a)—1-(N-(2-(Diethylamino)ethyl)-N-(4-(4-trifluoromethylphenyl)benzyl)-aminocarbonylmethyl)-2-(4-fluorobenzyl)thio-5,6-trimethylenepyrimidin-4-one

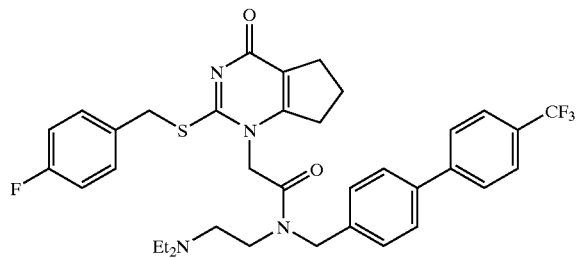

Intermediate B69 (87.1 g, 0.26 mol.) was suspended in dichloromethane (2.9 liter). 1-Hydroxybenzotriazole hydrate (35.2 g, 0.26 mol.) and 1-(3-dimethylaminopropyl)-3-ethylcarbodiimide hydrochloride (99.7 g, 0.52 mol.) were added and the suspension stirred for 45 minutes by which time complete solution had been obtained. Intermediate A30 (91.2 g, 0.26 mol.) was added as a solution in dichloromethane (100 ml) over 5 minutes and the solution stirred for 4 hours. Saturated ammonium chloride solution:water mixture (1:1, 1 liter) was added and the solution stirred for 10 minutes. The organic phase was separated and extracted with saturated ammonium chloride:water mixture (1:1, 1 liter), extracts were pH 6. The organic phase was separated and extracted with water (1 liter) containing acetic acid (10 ml), extract pH 5. The dichloromethane layer was separated and extracted with saturated sodium carbonate solution:water:saturated brine mixture (1:3:0.2, 1 liter), pH 10.5, then with saturated brine:water mixture (1:1, 1 liter). The brown solution was dried over anhydrous sodium sulfate in the presence of decolourising charcoal (35 g), filtered and the solvent removed in vacuo to give a dark brown foam.

The foam was dissolved in iso-propyl acetate (100 ml) and the solvent removed in vacuo. The dark brown gummy residue was dissolved in boiling iso-propyl acetate (500 ml), cooled to room temperature, seeded and stirred overnight. The pale cream solid produced was filtered off and washed with iso-propyl acetate (100 ml). The solid was sucked dry in the sinter for 1 hour then recrystallized from iso-propyl acetate (400 ml). After stirring overnight the solid formed was filtered off, washed with iso-propyl acetate (80 ml) and dried in vacuo to give the title compound, 110 g, 63.5% yield. 1H NMR (CDCl$_3$, ca 1.9:1 rotamer mixture) δ 0.99 (6H, t), 2.10 (2H, m), 2.50 (4H, q), 2.58/2.62 (2H, 2 ×t), 2.70/2.82 (2H, 2 ×t), 2.86 (2H, t), 3.28/3.58 (2H, 2×t), 4.45/4.52 (2H, 2×s), 4.68/4.70 (2H, 2×s), 4.93 (2H, s), 6.95 (2H, m), 7.31 (2H, d), 7.31/7.37 (2H, 2×m), 7.48/7.52 (2H, d), 7.65 (2H, m), 7.72 (2H, m); MS (APCI) (M+H)$^+$ 667; mp 125° C. (by DSC—assymetric endotherm).

Example 3(b)—1-(N-(2-(Diethylamino)ethyl)-N-(4-(4-trifluoromethylphenyl)benzyl)-aminocarbonylmethyl)-2-(4-fluorobenzyl)thio-5,6-trimethylenepyrimidin-4-one Bitartrate Prepared from intermediates A30 and B69 by the method of Example 1. $^1$H-NMR (d$_6$-DMSO, ca 1:1 rotamer mixture) δ 0.92/0.99 (6H, 2×t), 1.99 (2H, m), 2.54 (6H, m), 2.68/2.74 (4H, m), 3.36 (2H, m), 4.21 (2H, s), 4.37/4.44 (2H, 2×s), 4.63/4.74 (2H, 2×s), 4.89/5.13 (2H, 2×s), 7.08/7.14 (2H, 2×m), 7.36–7.50 (4H, m), 7.64/7.70 (2H, 2×d), 7.83 (4H, m); MS (APSI+) found (M+1)=667; C$_{36}$H$_{38}$F$_4$N$_4$O$_2$S requires 666.

Example 3(c)—1-(N-(2-(Diethylamino)ethyl)-N-(4-(4-trifluoromethylphenyl)benzyl)-aminocarbonylmethyl)-2-(4-fluorobenzyl)thio-5,6-trimethylenepyrimidin-4-one Hydrochloride The free base from Example 3(a) (3.00 g, 0.0045 mol) was suspended with stirring in isopropanol (30 ml) and warmed to 45° C. to give a clear solution. The solution was then cooled to ambient temperature and conc. hydrochloric acid (0.40 ml, 0.045 mol) was added. The resultant slurry was then stirred at ambient temperature for 35 minutes, before being cooled to 0° C. for 35 minutes. The slurry was then filtered and washed with isopropanol (10 ml), followed by heptane (30 ml), before being dried under vacuum to give the title compound as a white solid (3.00 g, 95%). $^1$H NMR (CDCl$_3$) δ 1.38 (6H, t), 2.08 (2H, m), 2.82 (2H, t), 2.99 (2H, t), 3.19 (4H, m), 3.35 (2H, m), 3.97 (2H, s), 4.42 (2H, s), 4.81 (2H, s), 4.99 (2H, s), 6.87 (2H, t), 7.26 (2H, t), 7.33 (2H, d), 7.41 (2H, d), 7.53 (2H, d), 7.71 (2H, d), 11.91 (1H, s).

Example 4—1-(N-(2-(Diethylamino)ethyl)-N-(2-(4-trifluoromethylphenyl)pyrid-5-yl-methyl) aminocarbonylmethyl)-2-(4-fluorobenzyl)thio-5,6-trimethylenepyrimidin-4-one Bitartrate

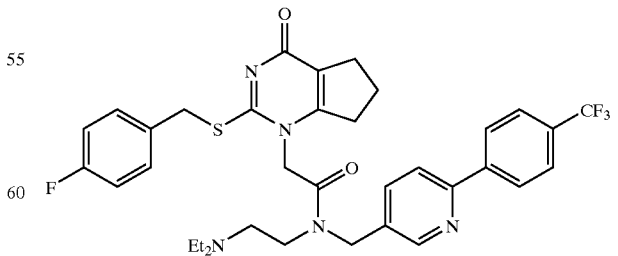

Prepared from intermediates A31 and B69 by the method of Example 1. $^1$H-NMR (d$_6$-DMSO, ca 3:1 rotamer mixture) δ 0.92/0.98 (6H, t), 1.99 (2H, m), 2.53 (6H, m), 2.68/2.75

(4H, m), 3.41 (2H, m), 4.22 (2H, s), 4.37/4.42 (2H, 2×s), 4.66/4.79 (2H, 2×s), 4.93/5.13 (2H, 2×s), 7.07/7.12 (2H, 2×t), 7.39/7.47 (2H, 2×t), 7.77/7.86 (1H, 2×dd), 7.87 (2H, d), 7.98/8.05 (1H, 2×dd), 8.28 (2H, d), 8.61/8.69 (1H, 2×s); MS (APCI+) found (M+1)=668; $C_{35}H_{37}F_4N_5O_2S$ requires 667.

Example 5—1-(N-(2-(Diethylamino)ethyl)-N-(2-(4-trifluoromethylphenyl)pyrimid-5-yl-ethyl) aminocarbonylmethyl)-2-(4-fluorobenzyl)thio-5,6-trimethylenepyrimidin-4-one Bitartrate

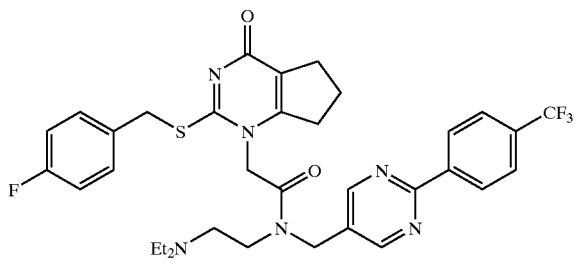

Prepared from intermediates A33 and B69 by the method of Example 1. $^{1}$H-NMR ($d_6$-DMSO, ca 3:1 rotamer mixture) δ 0.92/1.09 (6H, t), 1.96 (2H, m), 2.60 (6H, m), 2.75 (4H, m), 3.48 (2H, m), 4.23 (2H, s), 4.38/4.40 (2H, 2×s), 4.65/4.81 (2H, 2×s), 4.97/5.11 (2H, 2×s), 7.07/7.10 (2H, 2×t), 7.38/7.44 (2H, 2×t), 7.91 (2H, d), 8.57 (2H, d), 8.84/8.93 (2H, 2×s); MS (APCI+) found (M+1)=669; $C_{34}H_{36}F_4N_6O_2S$ requires 668.

Example 6—1-(N-Methyl-N-(2-(4-chlorophenyl) benzyl)aminocarbonylmethyl)-2-(4-fluorobenzyl) thio-5-(2-aminoethyl)pyrimidin-4-one Hydrochloride

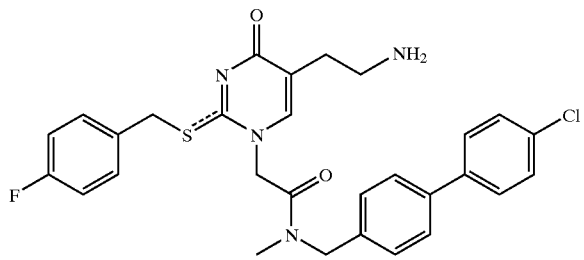

A solution of Intermediate B80 (0.228 g) in ethanol (20 ml) was hydrogenated over 10% palladium on charcoal (0.09 g) at atmospheric pressure for 2 days. The catalyst was filtered off, the solvent was removed in vacuo, and the resulting oil was purified by chromatography (silica, 10% methanolic ammonia in dichloromethane). The free base was dissolved in dichloromethane (5 ml), and an equimolar quantity of hydrogen chloride in ether added. The solvent was removed in vacuo, and the residue triturated with ether; yield 0.132 g). $^{1}$H-NMR ($d_6$-DMSO, ca 2:1 rotamer mixture) δ 2.58 (2H, m), 2.87/2.99 (3H, 2×s), 2.99 (2H, m), 4.40/4.45 (2H, 2×s), 4.57/4.66 (2H, 2×s), 4.97/5.00 (2H, 2×s), 7.16 (2H, m), 7.33/7.38 (2H, 2×d), 7.4–7.7 (9H, m), 8.0 (2H, br m); MS (APCI+) found (M+1)=551/553; $C_{29}H_{28}ClFN_4O_2S$ requires 550/552.

Example 7—1-(N-Methyl-N-(2-(4-chlorophenyl) benzyl)aminocarbonylmethyl)-2-(4-fluorobenzyl) thio-5-(2-acetamidoethyl)pyrimidin-4-one

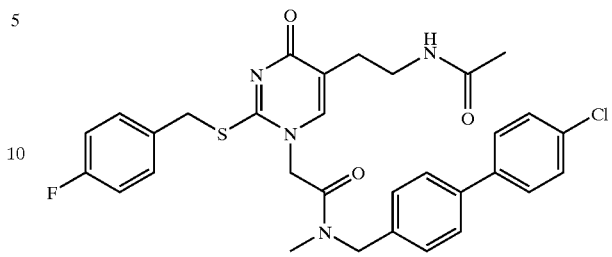

A solution of Example 6 (0.173 g, 1 equiv), acetic anhydride (0.033 ml, 1.1 equiv) and diisopropylamine (0.066 ml, 1.2 equiv) in dichloromethane (10 ml) was stirred at room temperature overnight. The solution was washed with aq. ammonium chloride and aq. sodium bicarbonate, then the organic layer was dried and evaporated. The residue was triturated with ether to obtain the title compound as a white solid (0.156 g). $^{1}$H-NMR (CDCl$_3$, ca 2:1 rotamer mixture) δ 1.96 (3H, s), 2.64 (2H, m), 2.96/3.10 (3H, 2×s), 3.49 (2H, m), 4.46–4.64 (6H, m), 6.77 (1H, br t), 6.97–7.16 (3H, m), 7.26–7.49 (10H, m); MS (APCI+) found (M+1)= 593/595; $C_{31}H_{30}ClFN_4O_3S$ requires 592/594.

Example 8—1-(N-(2-(Diethylamino)ethyl)-N-(2-(4-chlorophenyl)benzyl)aminocarbonylmethyl)-2-(4-fluorobenzyl)thio-5-(dimethylaminomethyl) pyrimidin-4-one

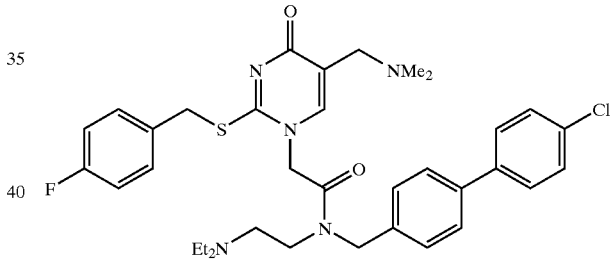

Methanesulfonic anhydride (0.134 g, 1.2 equiv) was added to a solution of Example 37 (0.40 g, 1 equiv) and triethylamine (0.124 ml, 1.4 equiv) in dichloromethane (5 ml) at 0° C., then stirred at this temperature for 4 hours. The mixture was washed with water, dried and evaporated to yield the mesylate as a pale yellow solid. This was dissolved in a 2M solution of dimethylamine in THF (10 ml) and stirred at room temperature for 16 hours. The solvent and excess dimethylamine was removed in vacuo, and the product was purified by chromatography (silica, 5–20% methanol in ethyl acetate, then 1–10% methanolic ammonia in dichloromethane) to obtain the title compound. $^{1}$H-NMR (CDCl$_3$) δ 0.98 (6H, t), 2.28/2.30 (each 3H, s), 2.46–2.65 (6H, m), 3.26/3.56 (2H, 2×t), 3.33/3.36 (2H, 2×s), 4.46/4.53/5.54/4.90 (4H, 4×s), 4.67 (2H, s), 6.98 (2H, m), 7.21–7.50 (1H, m); MS (APCI+) found (M+1)=650/652; $C_{35}H_{41}ClFN_5O_2S$ requires 649/651.

The following Examples were made by the method of Example 1 except that in a few cases EDC (2 equiv) and hydroxybenzotriazole (1 equiv) were used in place of HATU and diisopropylamine, in an essentially similar procedure. Where indicated, the salts were subsequently prepared by the methods of Examples 1 or 6 as appropriate:

| Ex. No. | Precursors | Structure | Name |
|---|---|---|---|
| 20 | Int. A3<br>Int. B60 | 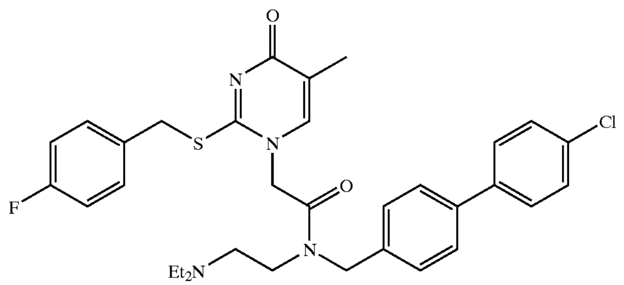 | 1-(N-(2-(Diethylamino)ethyl)-N-(4-(4-chlorophenyl)benzyl)aminocarbonyl-methyl)-2-(4-fluorobenzyl)thio-5-methylpyrimidin-4-one hydrochloride |
| 21 | Int. A26<br>Int. B60 | 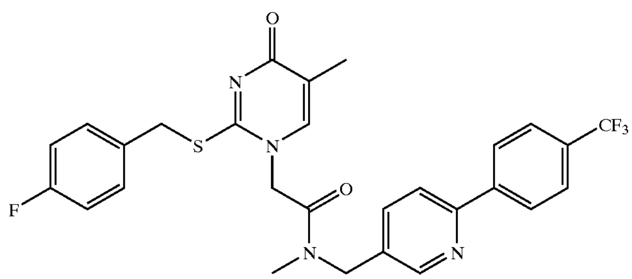 | 1-(N-methyl-N-(2-(4-trifluoromethyl-phenyl)pyrid-5-ylmethyl)amino-carbonylmethyl)-2-(4-fluorobenzyl)thio-5-methylpyrimidin-4-one bitartrate |
| 22 | Int. A30<br>Int. B60 | 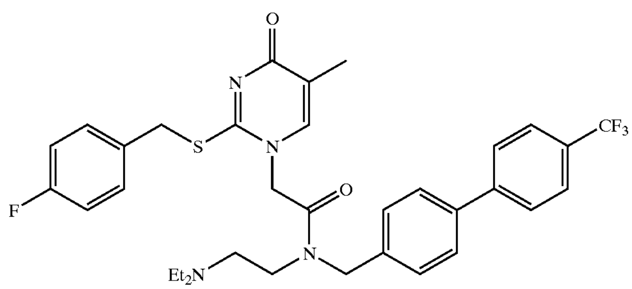 | 1-(N-(2-(Diethylamino)ethyl)-N-(4-(4-trifluoromethylphenyl)benzyl)-amino-carbonylmethyl)-2-(4-fluorobenzyl)thio-5-methylpyrimidin-4-one bitartrate |
| 23 | Int. A31<br>Int. B60 | 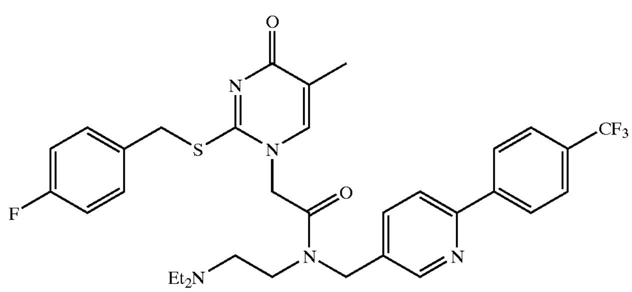 | 1-(N-(2-(Diethylamino)ethyl)-N-(2-(4-trifluoromethylphenyl)pyrid-5-yl-methyl)aminocarbonyl-methyl)-2-(4-fluorobenzyl)thio-5-methylpyrimidin-4-one bitartrate |
| 24 | Int. A32<br>Int. B60 | 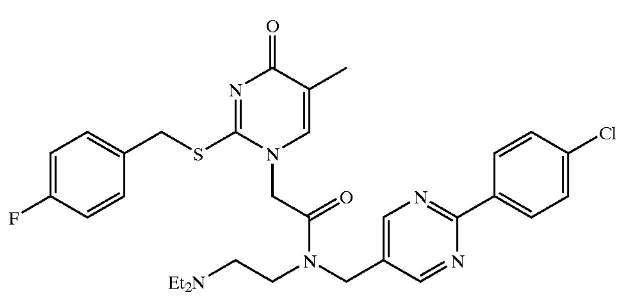 | 1-(N-(2-Diethylamino)ethyl)-N-(2-(4-chlorophenyl)pyrimid-5-yl-methyl)-aminocarbonyl-methyl)-2-(4-fluoro-benzyl)thio-5-methylpyrimidin-4-one bitartrate |

-continued

| Ex. No. | Precursors | Structure | Name |
|---|---|---|---|
| 25 | Int. A33<br>Int. B60 | 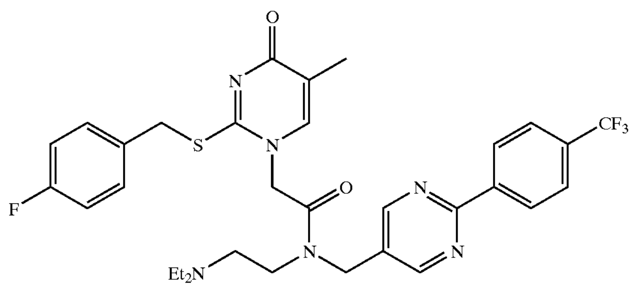 | 1-(N-(2-Diethylamino)ethyl)-N-(2-(4-trifluoromethylphenyl)pyrimid-5-yl-methyl)aminocarbonyl-methyl)-2-(4-fluorobenzyl)thio-5-methylpyrimidin-4-one bitartrate |
| 26 | Int. A35<br>Int. B60 | 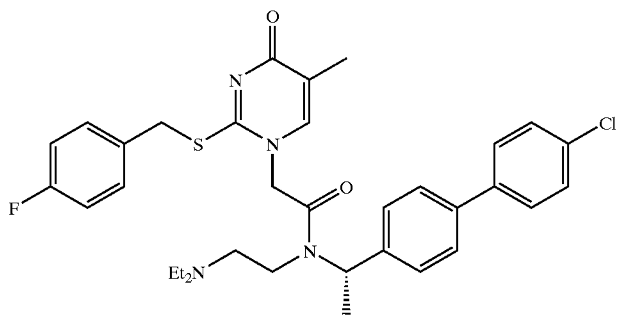 | (±)-1-(N-(2-(Diethylamino)ethyl)-N-(1-(4-(4-chlorophenyl)phenyl)ethyl)-aminocarbonyl-methyl)-2-(4-fluoro-benzyl)thio-5-methylpyrimidin-4-one bitartrate |
| 27 | Int. A34<br>Int. B60 | 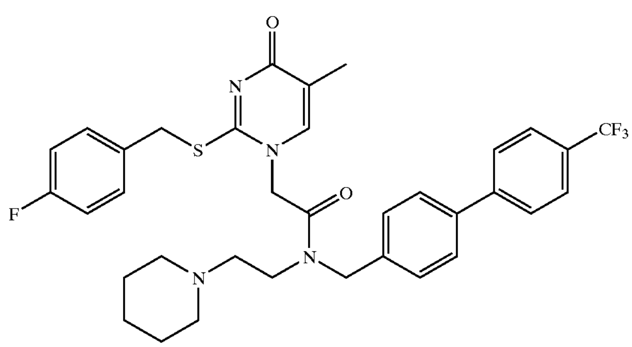 | 1-(N-(2-(1-piperidino)ethyl)-N-(4-(4-trifluoromethylphenyl)benzyl)-amino-carbonyl-methyl)-2-(4-fluorobenzyl)-thio-5-methylpyrimidin-4-one bitartrate |
| 28 | Int. A25<br>Int. B62 | 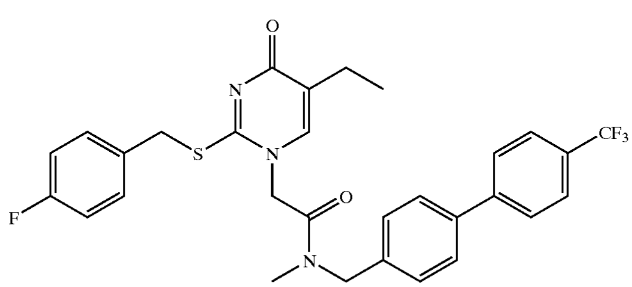 | 1-(N-methyl-N-(4-(4-trifluoromethyl-phenyl)benzyl)-aminocarbonyl-methyl)-2-(4-fluorobenzyl)thio-5-ethylpyrimidin-4-one |
| 29 | Int. A3<br>Int. B62 | 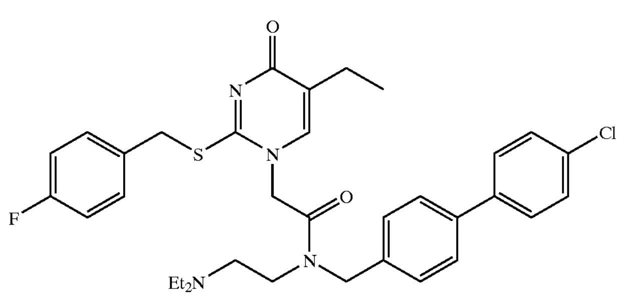 | 1-(N-(2-(Diethylamino)ethyl)-N-(4-(4-chlorophenyl)benzyl)-aminocarbonyl-methyl)-2-(4-fluorobenzyl)thio-5-ethyl-pyrimidin-4-one bitartrate |

| Ex. No. | Precursors | Structure | Name |
|---|---|---|---|
| 30 | Int. A26<br>Int. B62 | (structure) | 1-(N-methyl-N-(2-(4-trifluoromethyl-phenyl)pyrid-5-yl-methyl)-amino-carbonyl-methyl)-2-(4-fluorobenzyl)-thio-5-ethyl-pyrimidin-4-one |
| 31 | Int. A32<br>Int. B62 | (structure) | 1-(N-(2-(Diethylamino)ethyl-N-(2-(4-chlorophenyl)pyrimid-5-yl-methyl)-aminocarbonyl-methyl)-2-(4-fluoro-benzyl)thio-5-ethylpyrimidin-4-one bitartrate |
| 32 | Int. A33<br>Int. B62 | (structure) | 1-(N-(2-(Diethylamino)ethyl)-N-(2-(4-trifluoromethylphenyl)pyrimid-5-yl-methyl)aminocarbonylmethyl)-2-(4-fluorobenzyl)thio-5-ethylpyrimidin-4-one bitartrate |
| 33 | Int. A3<br>Int. B63 | (structure) | 1-(N-(2-(Diethylamino)ethyl)-N-(4-(4-chlorophenyl)benzyl)-aminocarbonyl-methyl)-2-(4-fluorobenzyl)thio-5-propylpyrimidin-4-one bitartrate |
| 34 | Int. A30<br>Int. B63 | (structure) | 1-(N-(2-(Diethylamino)ethyl)-N-(4-(4-trifluoromethylphenyl)benzyl)-amino-carbonyl-methyl)-2-(4-fluorobenzyl)-thio-5-propylpyrimidin-4-one bitartrate |

-continued

| Ex. No. | Precursors | Structure | Name |
|---|---|---|---|
| 35 | Int. A30<br>Int. B64 | 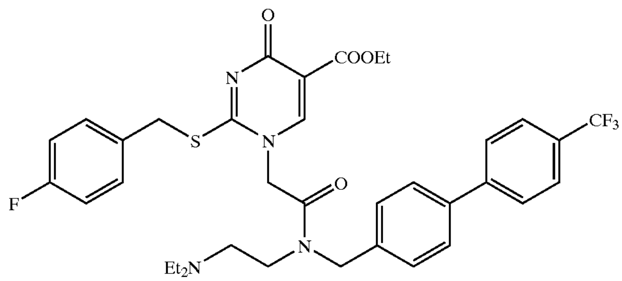 | 1-(N-(2-(Diethylamino)ethyl)-N-(4-(4-trifluoromethylphenyl)benzyl)-aminocarbonyl-methyl)-2-(4-fluorobenzyl)thio-5-ethoxycarbonylmethyl-pyrimidin-4-one bitartrate |
| 36 | Int. A30<br>Int. B65 | 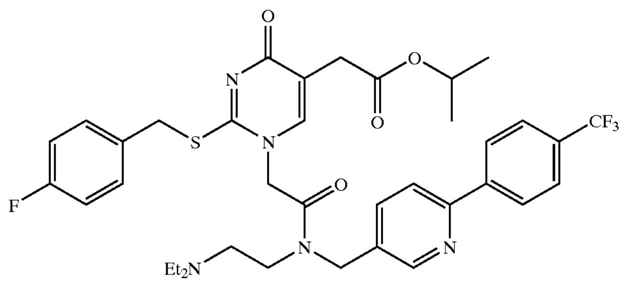 | 1-(N-(2-(Diethylamino)ethyl)-N-(4-(4-trifluoromethylphenyl)benzyl)aminocarbonylmethyl)-2-(4-fluorobenzyl)thio-5-isopropoxycarbonylmethylpyrimidin-4-one bitartrate |
| 37 | Int. A3<br>Int. B66 | 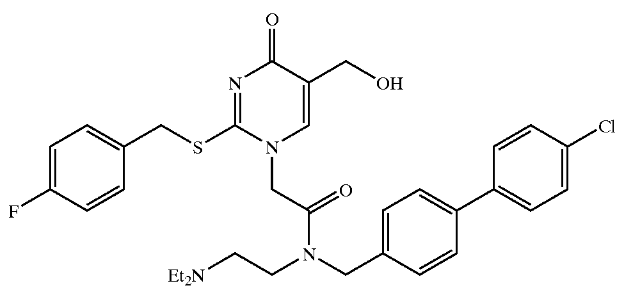 | 1-(N-(2-(Diethylamino)ethyl)-N-(4-(4-chlorophenyl)benzyl)-aminocarbonyl-methyl)-2-(4-fluorobenzyl)thio-5-hydroxymethylpyrimidin-4-one bitartrate |
| 38 | Int. A30<br>Int. B66 | 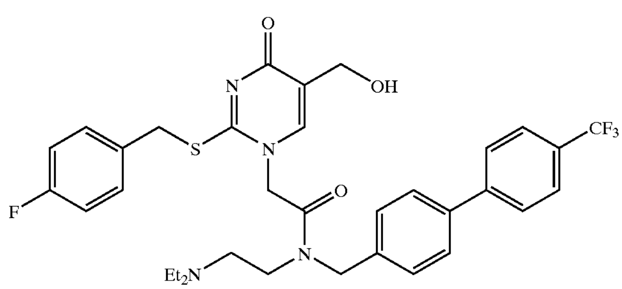 | 1-(N-(2-(Diethylamino)ethyl)-N-(4-(4-trifluoromethylphenyl)benzyl)-aminocarbonyl-methyl)-2-(4-fluorobenzyl)-thio-5-hydroxymethylpyrimidin-4-one bitartrate |
| 39 | Int. A2<br>Int. B67 | 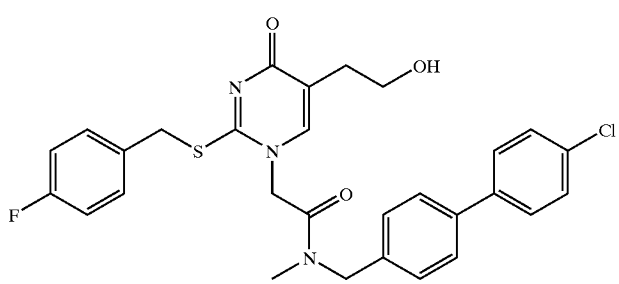 | 1-(N-methyl-N-(4-(4-chlorophenyl)-benzyl)-aminocarbonyl-methyl)-2-(4-fluorobenzyl)thio-5-(2-hydroxyethyl)-pyrimidin-4-one bitartrate |

-continued

| Ex. No. | Precursors | Structure | Name |
|---|---|---|---|
| 40 | Int. A3<br>Int. B67 | 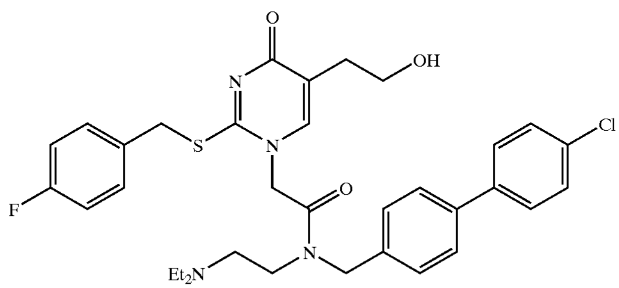 | 1-(N-(2-(Diethylamino)ethyl)-N-(4-(4-chlorophenyl)benzyl)-aminocarbonyl-methyl)-2-(4-fluorobenzyl)thio-5-(2-hydroxyethyl)pyrimidin-4-one bitartrate |
| 41 | Int. A31<br>Int. B67 | 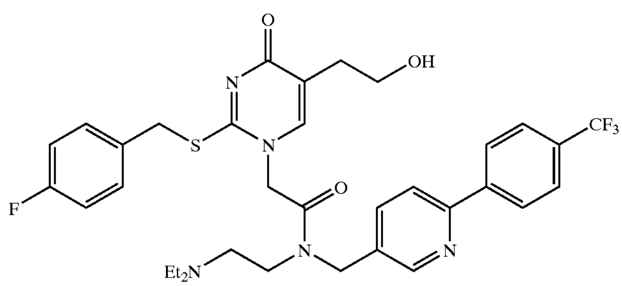 | 1-(N-(2-(Diethylamino)ethyl)-N-(2-(4-trifluoromethylphenyl)pyrid-5-yl-methyl)aminocarbonyl-methyl)-2-(4-fluorobenzyl)thio-5-(2-hydroxyethyl)-pyrimidin-4-one bitartrate |
| 42 | Int. A30<br>Int. B67 | 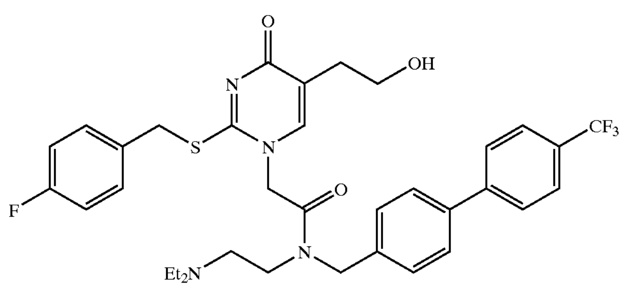 | 1-(N-(2-(Diethylamino)ethyl)-N-(4-(4-trifluoromethylphenyl)benzyl)amino-carbonyl-methyl)-2-(4-fluorobenzyl)-thio-5-(2-hydroxyethyl)pyrimidin-4-one bitartrate |
| 43 | Int. A30<br>Int. B68 | 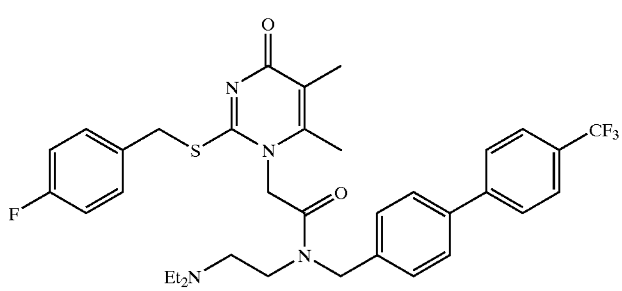 | 1-(N-(2-(Diethylamino)ethyl)-N-(4-(4-trifluoromethylphenyl)benzyl)amino-carbonyl-methyl)-2-(4-fluorobenzyl)-thio-5,6-dimethylpyrimidin-4-one bitartrate |
| 44 | Int. A3<br>Int. B69 | 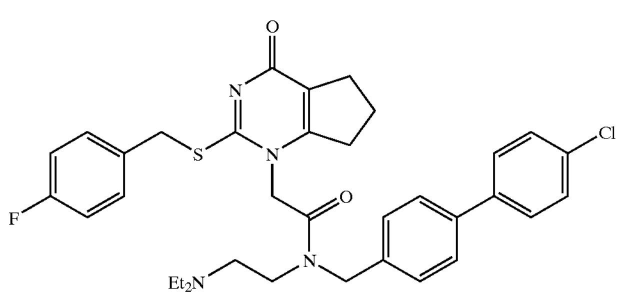 | 1-(N-(2-(Diethylamino)ethyl)-N-(4-(4-chlorophenyl)benzyl)aminocarbonyl-methyl)-2-(4-fluorobenzyl)thio-5,6-trimethylenepyrimidin-4-one bitartrate |

-continued

| Ex. No. | Precursors | Structure | Name |
|---|---|---|---|
| 45 | Int. A3<br>Int. B70 | 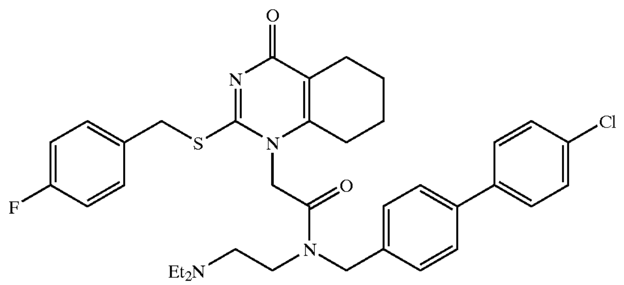 | 1-(N-(2-(Diethylamino)ethyl)-N-(4-(4-chlorophenyl)benzyl)-aminocarbonyl-methyl)-2-(4-fluorobenzyl)thio-5,6-tetramethylenepyrimidin-4-one bitartrate |
| 46 | Int. A30<br>Int. B70 | 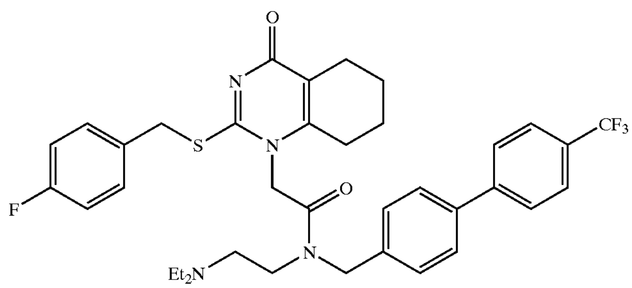 | 1-(N-(2-(Diethylamino)ethyl)-N-(4-(4-trifluoromethylphenyl)benzyl)amino-carbonylmethyl)-2-(4-fluorobenzyl)thio-5,6-tetramethylenepyrimidin-4-one bitartrate |
| 47 | Int. A31<br>Int. B70 | 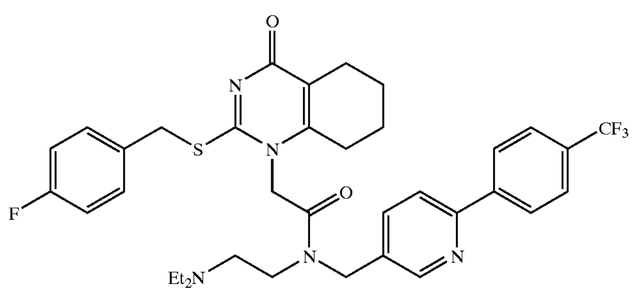 | 1-(N-(2-(Diethylamino)ethyl)-N-(2-(4-trifluoromethylphenyl)pyrid-5-yl-methyl)aminocarbonylmethyl)-2-(4-fluorobenzyl)thio-5,6-tetramethylene-pyrimidin-4-one bitartrate |
| 49 | Int. A30<br>Int. B71 | 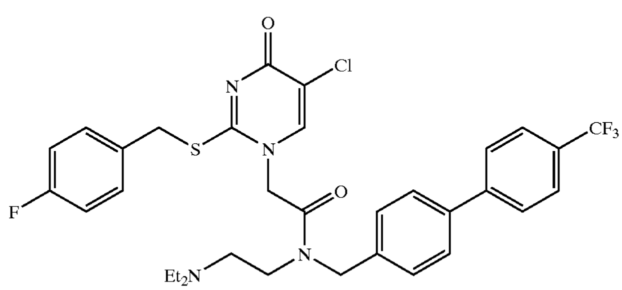 | 1-(N-(2-(Diethylamino)ethyl)-N-(4-(4-trifluoromethylphenyl)benzyl)amino-carbonyl-methyl)-2-(4-fluorobenzyl)-thio-5-chloropyrimidin-4-one bitartrate |
| 50 | Int. A3<br>Int. B71 | 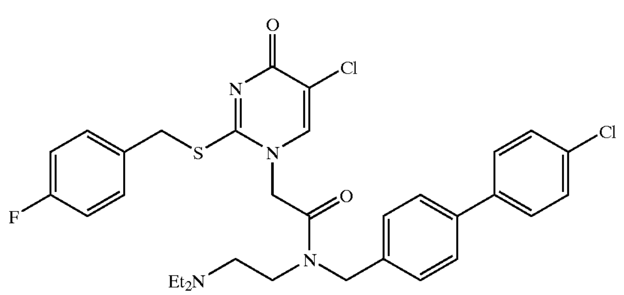 | 1-(N-(2-(Diethylamino)ethyl)-N-(4-(4-chlorophenyl)benzyl)-aminocarbonyl-methyl)-2-(4-fluorobenzyl)thio-5-chloropyrimidin-4-one bitartrate |

| Ex. No. | Precursors | Structure | Name |
|---|---|---|---|
| 51 | Int. A31<br>Int. B71 | 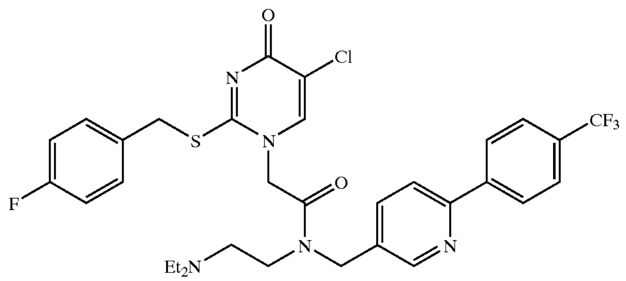 | 1-(N-(2-(Diethylamino)ethyl)-N-(2-(4-trifluoromethylphenyl)pyrid-5-yl-methyl)aminocarbonyl-methyl)-2-(4-fluorobenzyl)thio-5-chloropyrimidin-4-one bitartrate |
| 52 | Int. A30<br>Int. B72 | 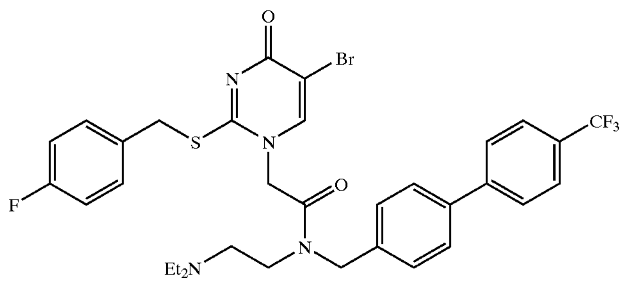 | 1-(N-(2-(Diethylamino)ethyl)-N-(4-(4-trifluoromethylphenyl)benzyl)amino-carbonyl-methyl)-2-(4-fluorobenzyl)-thio-5-bromopyrimidin-4-one bitartrate |
| 53 | Int. A3<br>Int. B72 | 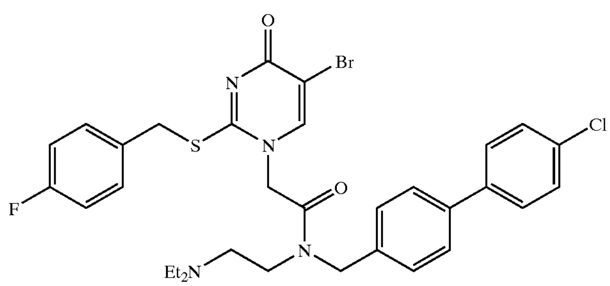 | 1-(N-(2-(Diethylamino)ethyl)-N-(4-(4-chlorophenyl)benzyl)-aminocarbonyl-methyl)-2-(4-fluorobenzyl)thio-5-bromopyrimidin-4-one bitartrate |
| 54 | Int. A30<br>Int. B73 | 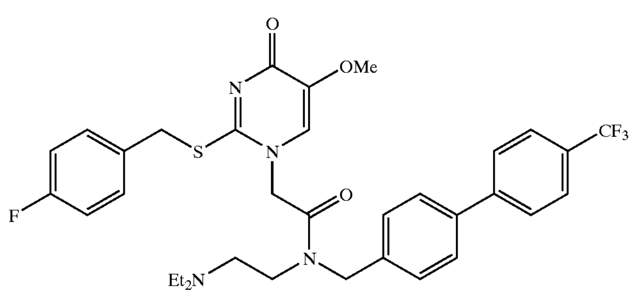 | 1-(N-(2-(Diethylamino)ethyl)-N-(4-(4-trifluoromethylphenyl)benzyl)amino-carbonylmethyl)-2-(4-fluorobenzyl)thio-5-methoxypyrimidin-4-one bitartrate |
| 55 | Int. A31<br>Int. B73 | 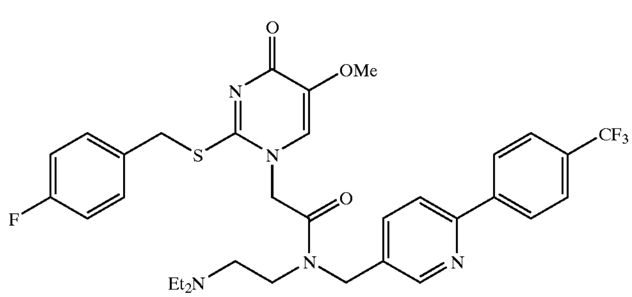 | 1-(N-(2-(Diethylamino)ethyl)-N-(2-(4-trifluoromethylphenyl)pyrid-5-yl-methyl)aminocarbonylmethyl)-2-(4-fluorobenzyl)thio-5-methoxypyrimidin-4-one bitartrate |

| Ex. No. | Precursors | Structure | Name |
|---|---|---|---|
| 56 | Int. A30<br>Int. B74 | 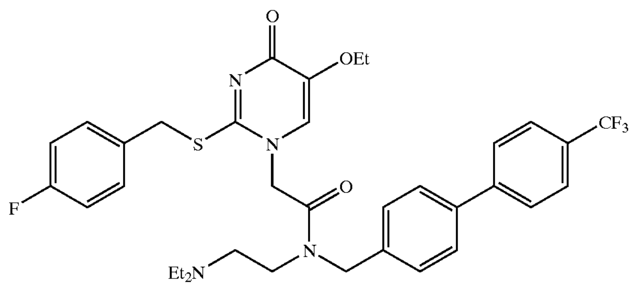 | 1-(N-(2-(Diethylamino)ethyl)-N-(4-(4-trifluoromethylphenyl)benzyl)aminocarbonylmethyl)-2-(4-fluorobenzyl)thio-5-ethoxypyrimidin-4-one bitartrate |
| 57 | Int. A31<br>Int. B74 | 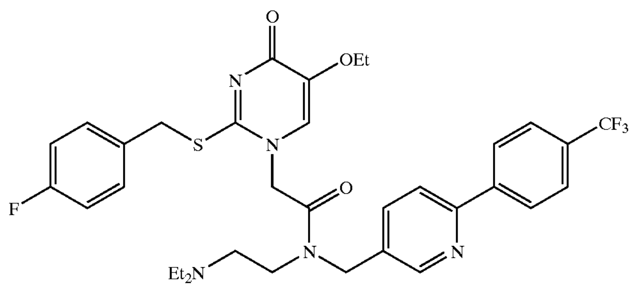 | 1-(N-(2-(Diethylamino)ethyl)-N-(2-(4-trifluoromethylphenyl)pyrid-5-yl-methyl)aminocarbonylmethyl)-2-(4-fluorobenzyl)thio-5-ethoxypyrimidin-4-one bitartrate |
| 58 | Int. A31<br>Int. B75 | 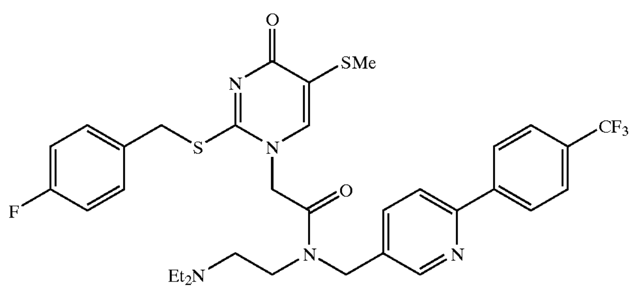 | 1-(N-(2-(Diethylamino)ethyl)-N-(2-(4-trifluoromethylphenyl)pyrid-5-yl-methyl)aminocarbonylmethyl)-2-(4-fluorobenzyl)thio-5-methylthio-pyrimidin-4-one bitartrate |
| 59 | Int. A30<br>Int. B75 | 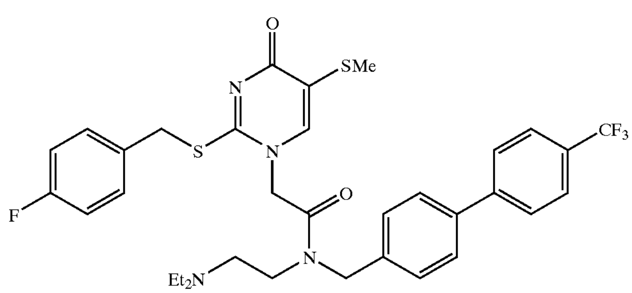 | 1-(N-(2-(Diethylamino)ethyl)-N-(4-(4-trifluoromethylphenyl)benzyl)aminocarbonylmethyl)-2-(4-fluorobenzyl)thio-5-methylthiopyrimidin-4-one bitartrate |
| 60 | Int. A30<br>Int. B76 | 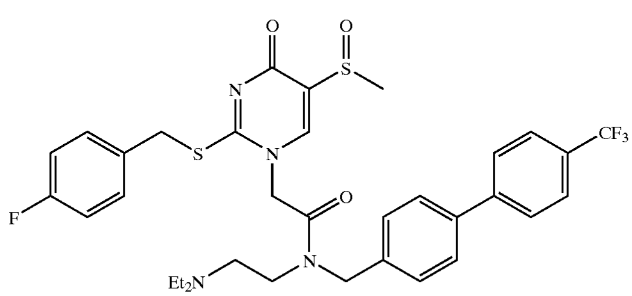 | 1-(N-(2-(Diethylamino)ethyl)-N-(4-(4-trifluoromethylphenyl)benzyl)aminocarbonylmethyl)-2-(4-fluorobenzyl)thio-5-methylsulfinylpyrimidin-4-one bitartrate |

-continued

| Ex. No. | Precursors | Structure | Name |
|---|---|---|---|
| 61 | Int. A31<br>Int. B76 | 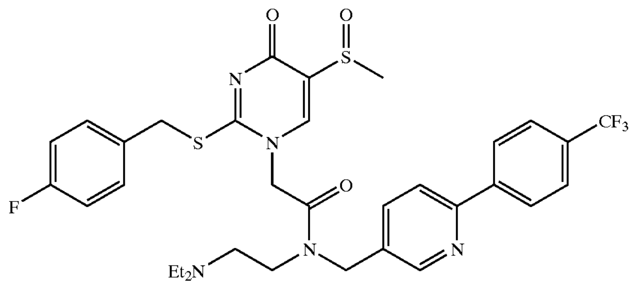 | 1-(N-(2-(Diethylamino)ethyl)-N-(2-(4-trifluoromethylphenyl)pyrid-5-yl-methyl)aminocarbonylmethyl)-2-(4-fluorobenzyl)thio-5-methylsulfinyl-pyrimidin-4-one bitartrate |
| 62 | Int. A30<br>Int. B177 | 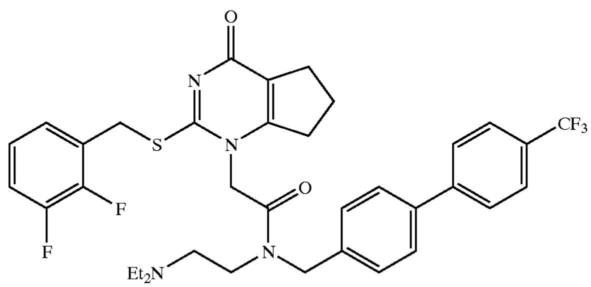 | 1-(N-(2-(Diethylamino)ethyl)-N-(4-(4-trifluoromethylphenyl)benzyl)amino-carbonylmethyl)-2-(2,3-difluorobenzyl)-thio-5,6-trimethylenepyrimidin-4-one bitartrate |
| 63 | Int. A30<br>Int. B178 | 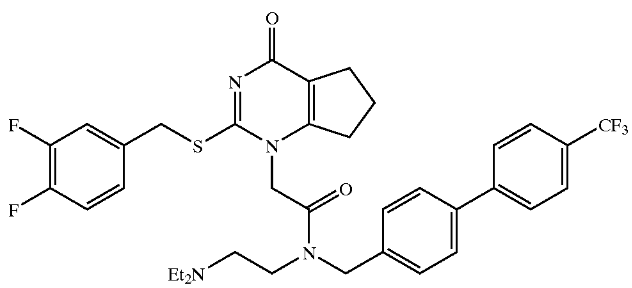 | 1-(N-(2-(Diethylamino)ethyl)-N-(4-(4-trifluoromethylphenyl)benzyl)amino-carbonylmethyl)-2-(3,4-difluorobenzyl)-thio-5,6-trimethylenepyrimidin-4-one bitartrate |
| 64 | Int. A30<br>Int. B179 | 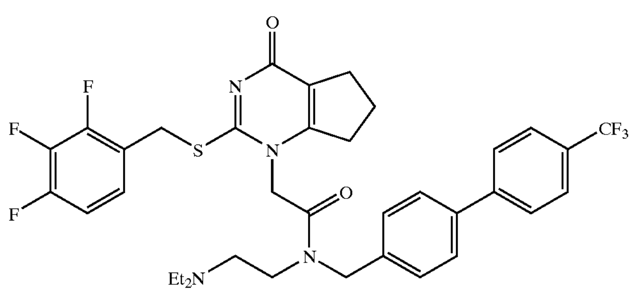 | 1-(N-(2-(Diethylamino)ethyl)-N-(4-(4-trifluoromethylphenyl)benzyl)amino-carbonylmethyl)-2-(2,3,4-trifluoro-benzyl)thio-5,6-trimethylenepyrimidin-4-one bitartrate |
| 65 | Int. A30<br>Int. B180 | 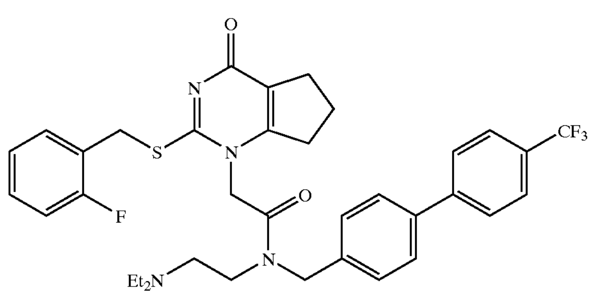 | 1-(N-(2-(Diethylamino)ethyl)-N-(4-(4-trifluoromethylphenyl)benzyl)amino-carbonylmethyl)-2-(2-fluorobenzyl)thio-5,6-trimethylenepyrimidin-4-one bitartrate |

-continued

| Ex. No. | Precursors | Structure | Name |
|---|---|---|---|
| 66 | Int. A25<br>Int. B69 | 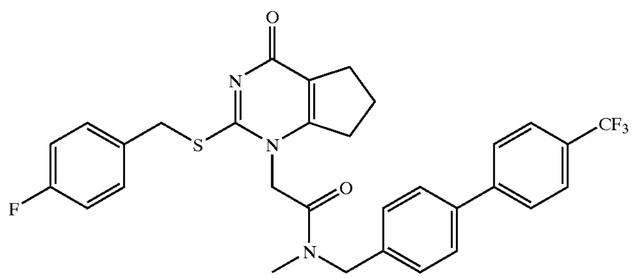 | 1-(N-methyl-N-(4-(4-trifluoromethyl-phenyl)benzyl)-aminocarbonylmethyl)-2-(4-fluorobenzyl)thio-5,6-trimethylene-pyrimidin-4-one |
| 67 | Int. A34<br>Int. B69 | 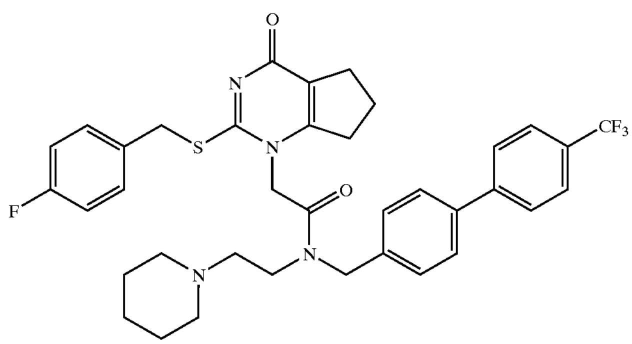 | 1-(N-(2-(1-piperidino)ethyl)-N-(4-(4-trifluoromethylphenyl)benzyl)amino-carbonylmethyl)-2-(4-fluorobenzyl)thio-5,6-trimethylenepyrimidin-4-one bitartrate |
| 68 | Int. A36<br>Int. B69 | 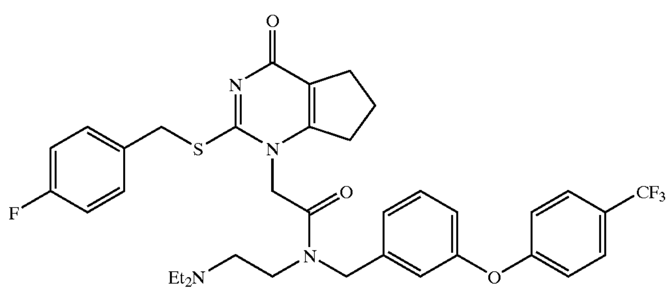 | 1-(N-(2-(Diethylamino)ethyl)-N-(3-(4-trifluoromethylphenoxy)benzyl)amino-carbonylmethyl)-2-(4-fluorobenzyl)thio-5,6-trimethylenepyrimidin-4-one |
| 69 | Int. A37<br>Int. B69 | 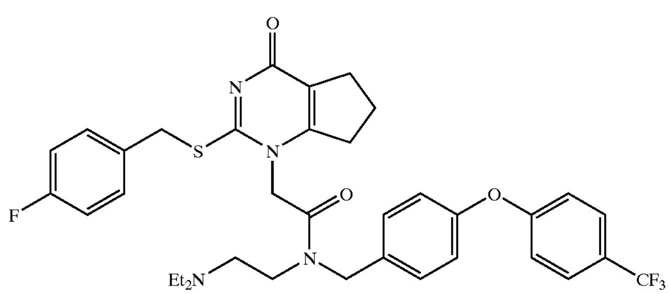 | 1-(N-(2-(Diethylamino)ethyl)-N-(4-(4-trifluoromethylphenoxy)benzyl)amino-carbonylmethyl)-2-(4-fluorobenzyl)thio-5,6-trimethylenepyrimidin-4-one bitartrate |
| 70 | Int. A39<br>Int. B69 | 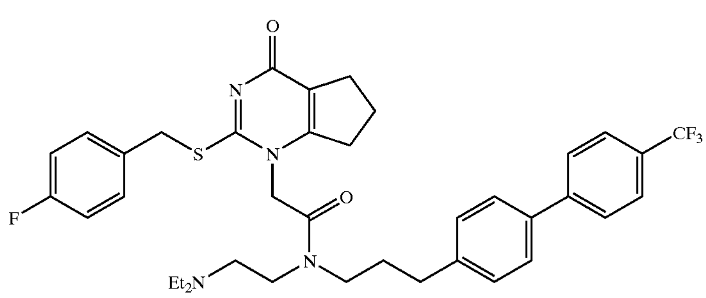 | 1-(N-(2-(Diethylamino)ethyl)-N-(4-(4-trifluoromethyl-biphenyl-4-yl)propyl)-aminocarbonylmethyl)-2-(4-fluoro-benzyl)thio-5,6-trimethylenepyrimidin-4-one |

-continued

| Ex. No. | Precursors | Structure | Name |
|---|---|---|---|
| 71 | Int. A39<br>Int. B62 | 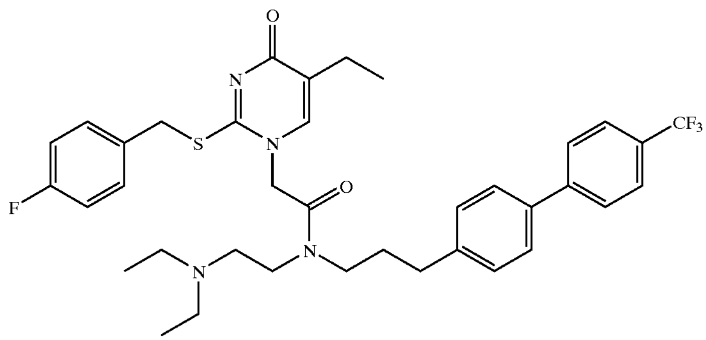 | 1-(N-(2-(Diethylamino)ethyl)-N-(4-(4-trifluoromethylbiphenyl-4-yl)propyl)-aminocarbonyl-methyl)-2-(4-fluoro-benzyl)thio-5-ethylpyrimidin-4-one |
| 72 | Int. A140<br>Int. B62 | 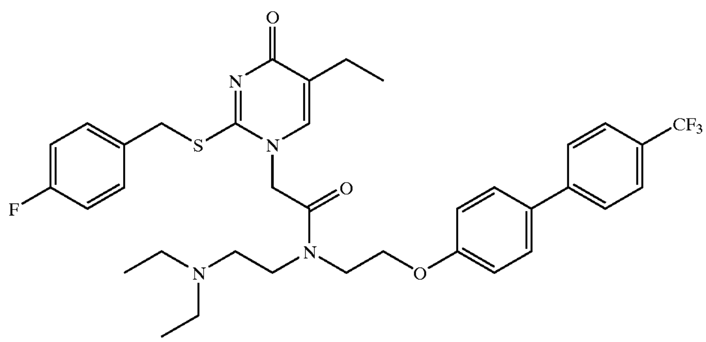 | 1-(N-(2-(Diethylamino)ethyl)-N-(4-(4-trifluoromethyl-biphenyl-4-yloxy)-ethyl)aminocarbonyl-methyl)-2-(4-fluorobenzyl)thio-5-ethylpyrimidin-4-one |
| 73 | Int. A18<br>Int. B69 | 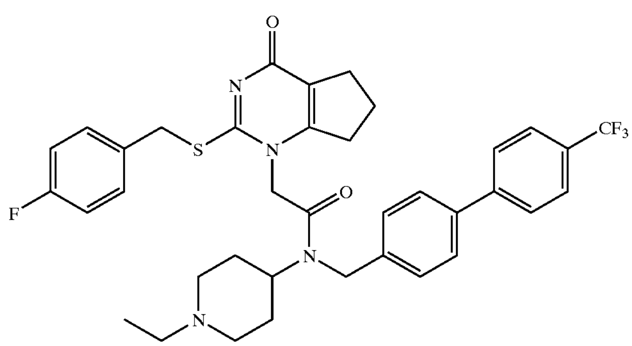 | 1-(N-(1-Ethylpiperidin-4-yl)-N-(4-(4-trifluoromethylphenyl)benzylamino-carbonylmethyl)-2-(4-fluorobenzyl)thio-5,6-trimethylenepyrimidin-4-one bitartrate |
| 74 | Int. A141<br>Int. B69 | 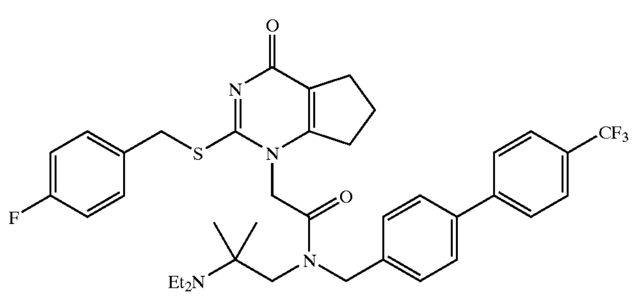 | 1-(N-(2-Ethylamino-2-methylpropyl)-N-(4-(4-trifluoromethylphenyl)benzyl)-aminocarbonylmethyl)-2-(4-fluoro-benzyl)thio-5,6-trimethylenepyrimidin-4-one bitartrate |

| Ex. No. | Precursors | Structure | Name |
|---|---|---|---|
| 75 | Int. A142<br>Int. B69 | 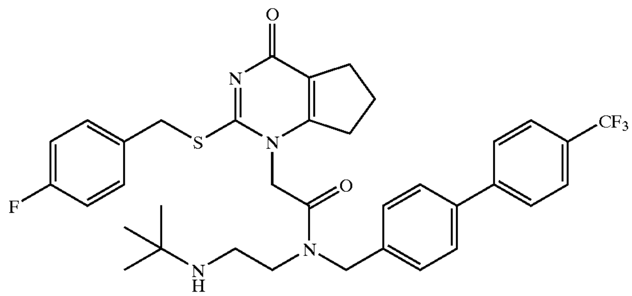 | N-(2-tert-butylaminoethyl)-N-(4-(4-trifluoromethylphenyl)benzyl)amino-carbonylmethyl)-2-(4-fluorobenzyl)thio-5,6-trimethylenepyrimidin-4-one bitartrate |
| 76 | Int. A30<br>Int. B181 | 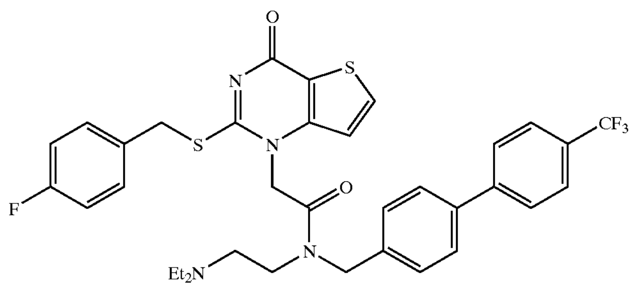 | N-(2-Diethylaminoethyl)-2-[2-(4-fluorobenzylthio)-4-oxo-4H-thieno[3,2-d]pyrimidin-1-yl]-N-(4'-trifluoro-methylbiphenyl-4-ylmethyl)-acetamide bitartrate |
| 77 | Int. A30<br>Int. B182 | 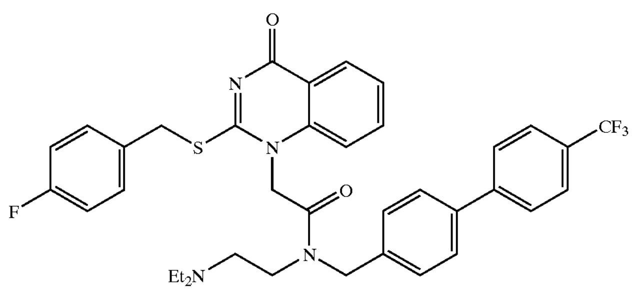 | N-(2-Diethylaminoethyl)-2-[2-(4-fluorobenzylthio)-4-oxo-4H-quinazolin-1-yl]-N-(4'-trifluoromethyl-biphenyl-4-ylmethyl)acetamide bitartrate |
| 78 | Int. A38<br>Int. B69 | 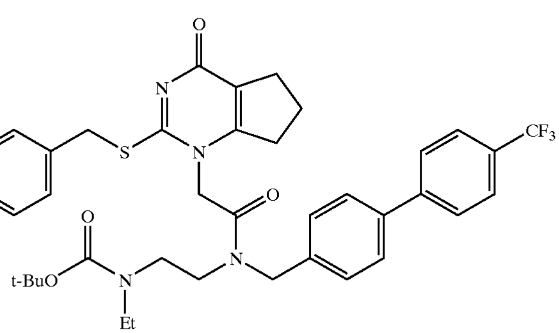 | Ethyl-{2-[{2-(4-fluorobenzyl-thio)-4-oxo-4,5,6,7-tetrahydro-cyclopentapyrimidin-1-yl]-ethanoyl}-{4'-trifluoromethylbiphenyl-4-yl-methyl)-amino]-ethyl}carbamic acid tert-butyl ester |
| 79 | Int. A60<br>Int. B69 | 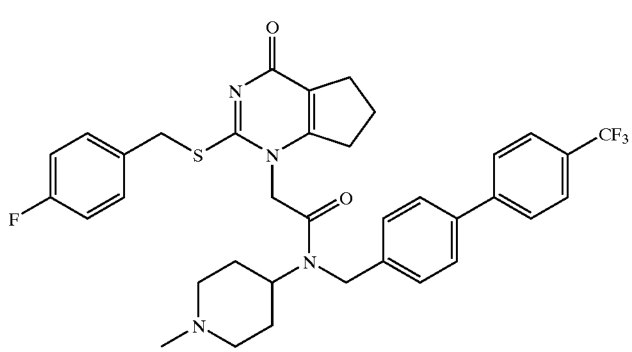 | 1-(N-(1-Methylpiperidin-4-yl)-N-(4-(4-trifluoromethylphenyl)benzyl)amino-carbonylmethyl)-2-(4-fluorobenzyl)thio-5,6-trimethylenepyrimidin-4-one bitartrate |

-continued

| Ex. No. | Precursors | Structure | Name |
|---|---|---|---|
| 80 | Int. A61<br>Int. B69 | 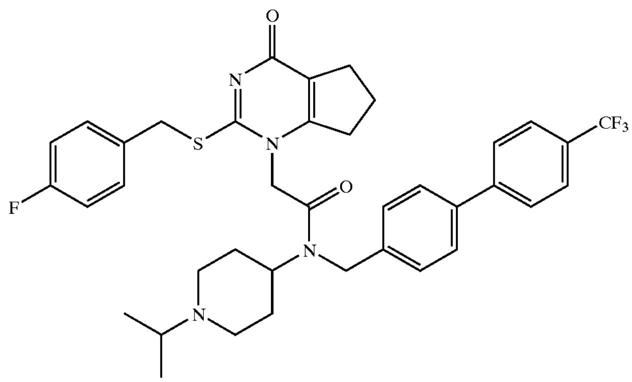 | 1-(N-(1-Isopropylpiperidin-4-yl)-N-(4-(4-trifluoromethylphenyl)benzyl)aminocarbonylmethyl)-2-(4-fluorobenzyl)thio-5,6-trimethylenepyrimidin-4-one bitartrate |
| 81 | Int. A62<br>Int. B69 | 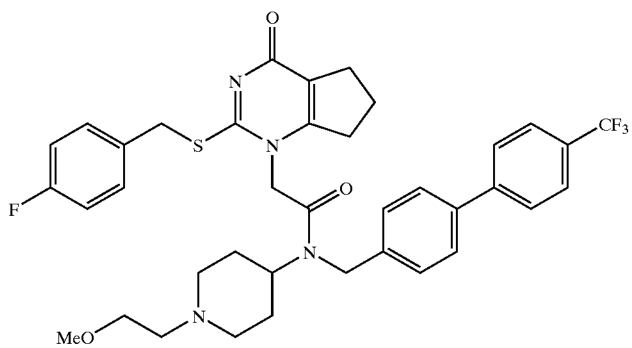 | 1-(N-(1-(2-Methoxyethyl)piperidin-4-yl)-N-(4-(4-trifluoromethylphenyl)-benzyl)aminocarbonylmethyl)-2-(4-fluorobenzyl)thio-5,6-trimethylene pyrimidin-4-one bitartrate |

The following compound was prepared by the method of Example 6:

| No. | Precursor | Structure | Name |
|---|---|---|---|
| 85 | Int. B81 | 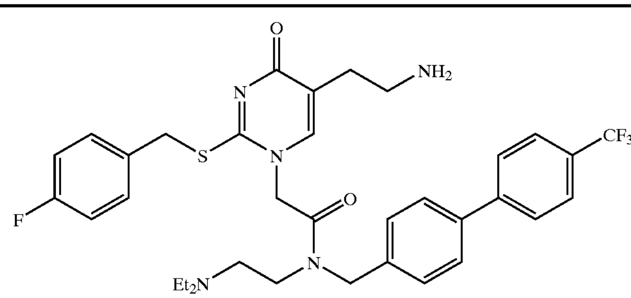 | 1-(N-(2-(Diethylamino)ethyl)-N-(4-(4-trifluoromethylphenyl)benzyl)aminocarbonylmethyl)-2-(4-fluorobenzyl)thio-5-(2-aminoethyl)pyrimidin-4-one bitartrate |

The following compounds were prepared by the method of Example 7:

| No. | Precursors | Structure | Name |
|---|---|---|---|
| 90 | Example 85, acetic anhydride | 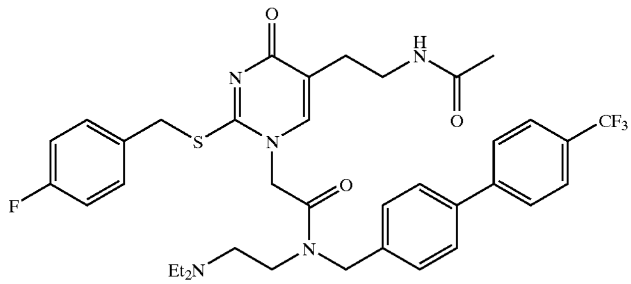 | 1-(N-(2-Diethylamino)ethyl)-N-(4-(4-trifluoromethylphenyl)benzyl)amino-carbonylmethyl)-2-(4-fluorobenzyl)thio-5-(2-acetamidoethyl)pyrimidin-4-one bitartrate |
| 91 | Example 85, methane-sulfonic anhydride | 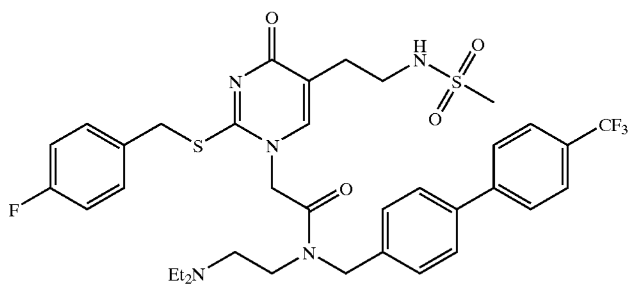 | 1-(N-(2-Diethylamino)ethyl)-N-(4-(4-trifluoromethylphenyl)benzyl)amino-carbonylmethyl)-2-(4-fluorobenzyl)thio-5-(2-methanesulfonamidoethyl)pyrimidin-4-one bitartrate |
| 92 | Example 85, methoxy-acetyl chloride | 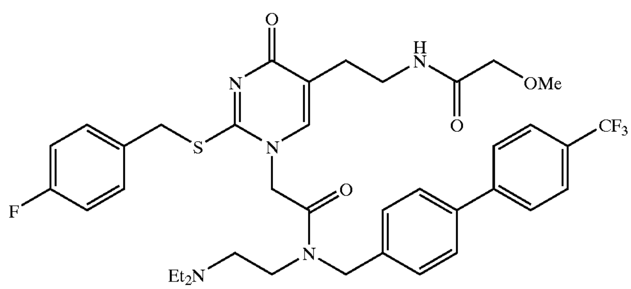 | 1-(N-(2-(Diethylamino)ethyl)-N-(4-(4-trifluoromethylphenyl)benzyl)amino-carbonylmethyl)-2-(4-fluorobenzyl)thio-5-(2-(methoxyacetamido)ethyl)pyrimidin-4-one bitartrate |

The following example was prepared by the method of Intermediate B60. The salt was prepared by the method of example 1:

| No. | Precursor | Structure | Name |
|---|---|---|---|
| 93 | Example 78 | 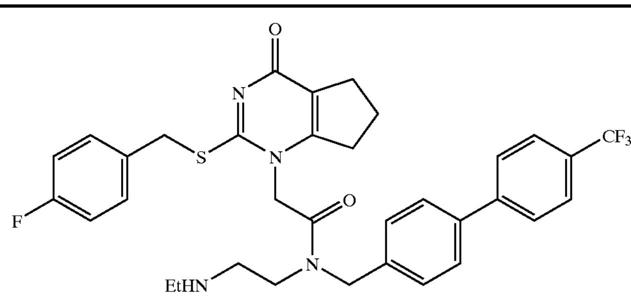 | 1-(N-(2-(Ethylamino)ethyl)-N-(4-(4-trifluoromethylphenyl)benzyl)-aminocarbonylmethyl)-2-(4-fluorobenzyl)thio-5,6-trimethylene-pyrimidin-4-one bitartrate |

Biological Data

1. Screen for Lp-PLA$_2$ Inhibition.

Enzyme activity was determined by measuring the rate of turnover of the artificial substrate (A) at 37 C. in 50 mM HEPES (N-2-hydroxyethylpiperazine-N'-2-ethanesulphonic acid) buffer containing 150 mM NaCl, pH 7.4.

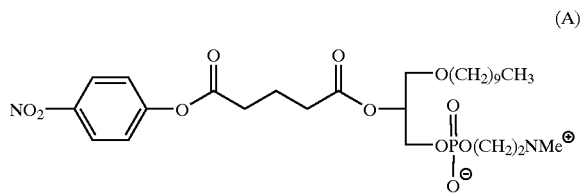

(A)

Assays were performed in 96 well titre plates.

Recombinant Lp-PLA$_2$ was purified to homogeneity from baculovirus infected Sf9 cells, using a zinc chelating column, blue sepharose affinity chromatography and an anion exchange column. Following purification and ultrafiltration, the enzyme was stored at 6 mg/ml at 4° C. Assay plates of compound or vehicle plus buffer were set up using automated robotics to a volume of 170 µl. The reaction was initiated by the addition of 20µl of 10×substrate (A) to give a final substrate concentration of 20 µM and 10 µl of diluted enzyme to a final 0.2 nM Lp-PLA$_2$. The reaction was followed at 405 nm and 37° C. for 20 minutes using a plate reader with automatic mixing. The rate of reaction was measured as the rate of change of absorbance.

Results

The compounds described in the Examples were tested as described above and had IC$_{50}$ values in the range <0.1 nM to 10 µM.

What is claimed is:

1. A compound which is 1-(N-(2-(diethylamino)ethyl)-N-(4-(4-trifluoromethylphenyl)benzyl)aminocarbonylmethyl)-2-(4-fluorobenzyl)thio-5,6-trimethylenepyrimidin-4-one, or a pharmaceutically acceptable salt thereof.

2. A pharmaceutical composition comprising a compound as claimed in claim 1 and a pharmaceutically acceptable carrier.

3. A composition according to claim 2 for oral administration.

* * * * *

UNITED STATES PATENT AND TRADEMARK OFFICE
CERTIFICATE OF CORRECTION

PATENT NO. : 6,649,619 B1 Page 1 of 1
DATED : November 18, 2003
INVENTOR(S) : Colin Andrew Leach, Stephen Allan Smith and Steven James Stanway It is certified that error appears in the above-identified patent and that said Letters Patent is hereby corrected as shown below:

<u>Title page,</u>
Item [75], Inventors, "Deirdre Mary Bernadette Hickey, Harlow(GB);
Robert John Ife, Harlow (GB);
Colin Andrew Leach, Harlow (GB);
Ivan Leo Pinto, Harlow (GB);
Stephen Allan Smith, Harlow (GB);
Steven James Stanway, Harlow (GB);"
should be -- Colin Andrew Leach, Harlow (GB);
Stephen Allan Smith, Harlow (GB);
Steven James Stanway, Harlow (GB);"--.

Signed and Sealed this

Twenty-fifth Day of May, 2004

JON W. DUDAS
*Acting Director of the United States Patent and Trademark Office*